US010201594B2

(12) United States Patent
Ruegg et al.

(10) Patent No.: US 10,201,594 B2
(45) Date of Patent: Feb. 12, 2019

(54) COMPOSITIONS AND METHODS FOR SAFE TREATMENT OF RHINITIS

(71) Applicant: Revance Therapeutics, Inc., Newark, CA (US)

(72) Inventors: Curtis L. Ruegg, Redwood City, CA (US); Hongran Fan Stone, Beijing (CN); Jacob M. Waugh, Palo Alto, CA (US)

(73) Assignee: Revance Therapeutics, Inc., Newark, CA (US)

( * ) Notice: Subject to any disclaimer, the term of this patent is extended or adjusted under 35 U.S.C. 154(b) by 0 days.

(21) Appl. No.: 15/155,551

(22) Filed: May 16, 2016

(65) Prior Publication Data

US 2016/0250302 A1 Sep. 1, 2016

Related U.S. Application Data

(63) Continuation of application No. 14/065,379, filed on Oct. 28, 2013.

(60) Provisional application No. 61/719,462, filed on Oct. 28, 2012.

(51) Int. Cl.

| *A61K 39/08* | (2006.01) |
| *A61K 39/00* | (2006.01) |
| *A61K 39/38* | (2006.01) |
| *A61K 38/48* | (2006.01) |
| *A61K 9/00* | (2006.01) |
| *A61K 47/10* | (2017.01) |
| *A61K 47/34* | (2017.01) |
| *A61K 47/42* | (2017.01) |
| *A61M 31/00* | (2006.01) |

(52) U.S. Cl.
CPC ........ *A61K 38/4893* (2013.01); *A61K 9/0043* (2013.01); *A61K 38/48* (2013.01); *A61K 47/10* (2013.01); *A61K 47/34* (2013.01); *A61K 47/42* (2013.01); *A61M 31/00* (2013.01); *C12Y 304/24069* (2013.01)

(58) Field of Classification Search
CPC ..... C61K 38/4893; A61K 39/08; A61K 38/00
See application file for complete search history.

(56) References Cited

U.S. PATENT DOCUMENTS

| 4,861,764 | A | 8/1989 | Samour et al. |
| 5,053,005 | A | 10/1991 | Borodic |
| 5,183,462 | A | 2/1993 | Borodic |
| 5,298,019 | A | 3/1994 | Borodic |
| 5,401,243 | A | 3/1995 | Borodic |
| 5,437,291 | A | 8/1995 | Pasricha et al. |
| 5,512,547 | A | 4/1996 | Johnson et al. |
| 5,562,907 | A | 10/1996 | Amon |
| 5,670,484 | A | 9/1997 | Binder |
| 5,674,205 | A | 10/1997 | Pasricha et al. |
| 5,683,713 | A | 11/1997 | Blank |
| 5,686,268 | A | 11/1997 | Alila |
| 5,696,077 | A | 12/1997 | Johnson et al. |
| 5,714,468 | A | 2/1998 | Binder |
| 5,766,605 | A * | 6/1998 | Sanders ............ A61K 38/4893 424/236.1 |
| 5,837,265 | A | 11/1998 | Montal et al. |
| 5,846,929 | A | 12/1998 | Johnson et al. |
| 6,063,768 | A | 5/2000 | First |
| 6,087,327 | A | 7/2000 | Pearce et al. |
| 6,113,915 | A | 9/2000 | Aoki et al. |
| 6,159,944 | A | 12/2000 | Fogel |
| 6,458,365 | B1 | 10/2002 | Aoki et al. |
| 6,645,501 | B2 | 11/2003 | Dowdy |
| 6,670,322 | B2 | 12/2003 | Goodnough et al. |
| 6,838,434 | B2 | 1/2005 | Voet |
| 6,896,992 | B2 | 5/2005 | Kearl |
| 6,974,578 | B1 | 12/2005 | Aoki et al. |
| 6,986,893 | B2 | 1/2006 | Aoki et al. |
| 7,060,498 | B1 | 6/2006 | Wang |
| 7,169,814 | B2 | 1/2007 | Rothbard et al. |
| 7,211,261 | B1 | 5/2007 | Moyer et al. |
| 7,288,259 | B2 | 10/2007 | Sanders et al. |
| 7,482,016 | B2 | 1/2009 | Dorr et al. |
| 7,537,773 | B1 | 5/2009 | Borodic |
| 7,608,275 | B2 | 10/2009 | Deem et al. |
| 7,655,243 | B2 | 2/2010 | Deem et al. |
| 7,655,244 | B2 | 2/2010 | Blumenfeld |
| 7,691,394 | B2 | 4/2010 | Borodic |

(Continued)

FOREIGN PATENT DOCUMENTS

| EP | 1421948 | 5/2004 |
| EP | 1 661 912 | 5/2006 |

(Continued)

OTHER PUBLICATIONS

Wen et al., Neuroimmunomodulation, 2007; 14: 78-83.*
Quillen et al., American Family Physician, 2006; 73(9):1583-90.*
http://www.animalresearch.info/en/designing-research/research-animals/guinea-pig/, accessed Oct. 1, 2017.*
Globe Newswire, Jun. 13, 2016; Revance Reports Results for RT001 Topical Phase 3 Trial for Lateral Canthal Lines; pp. 1-5 (Year: 2016).*
Agbottah et al., "Inhibition of HIV-1 Virus Replication Using Small Soluble Tat Peptides," Virology, 345(2), pp. 373-389, 2006.
Aoishi et al., "Treatment of allergic rhinitis with intranasal infusion of botulinum toxin type A in mice," Life Sciences, 147, pp. 132-136, 2016.

(Continued)

*Primary Examiner* — Gary B Nickol
*Assistant Examiner* — Lakia J Jackson-Tongue
(74) *Attorney, Agent, or Firm* — Kenneth Sonnenfeld; Nicci Fortune; King & Spalding LLP

(57) ABSTRACT

Methods for treating rhinitis in a subject are provided herein. The methods of the present invention comprise intranasal administration of a topical composition comprising a purified *botulinum* neurotoxin, a carrier and a viscosity modifier to one or more inner surfaces of the nose. The methods disclosed herein provide alternative methods for delivery of *botulinum* neurotoxin to the nasal anatomy for the treatment of rhinitis.

8 Claims, 4 Drawing Sheets

Specification includes a Sequence Listing.

(56) References Cited

U.S. PATENT DOCUMENTS

| | | |
|---|---|---|
| 7,691,974 B2 | 4/2010 | Steward et al. |
| 7,749,515 B2 | 7/2010 | Blumenfeld |
| 7,807,780 B2 | 10/2010 | Waugh et al. |
| 7,847,059 B2 | 12/2010 | O'Neal |
| 7,879,340 B2 | 2/2011 | Sanders |
| 7,879,341 B2 | 2/2011 | Taylor |
| 7,981,433 B2 | 7/2011 | Blumenfeld |
| 7,985,411 B2 | 7/2011 | Dolly |
| 8,022,179 B2 | 9/2011 | Dake et al. |
| 8,083,361 B2 | 12/2011 | Ide et al. |
| 8,088,360 B2 | 1/2012 | Sanders |
| 8,088,361 B2 | 1/2012 | Sanders |
| 8,092,781 B2 | 1/2012 | Sanders |
| 8,092,788 B2 | 1/2012 | Dake et al. |
| 8,105,817 B2 | 1/2012 | Deem et al. |
| 8,133,497 B2 | 3/2012 | Deem et al. |
| 8,173,138 B2 | 5/2012 | Moyer |
| 8,241,641 B2 | 8/2012 | Blumenfeld |
| 8,338,164 B2 | 12/2012 | Deem et al. |
| 8,349,292 B2 | 1/2013 | Sanders |
| 8,404,249 B2 | 3/2013 | Dake et al. |
| 8,530,425 B2 | 9/2013 | Blumenfeld |
| 8,557,255 B2 | 10/2013 | Marx et al. |
| 8,623,811 B2 | 1/2014 | Stone et al. |
| 8,636,684 B2 | 1/2014 | Deem et al. |
| 8,691,769 B2 | 4/2014 | Borodic |
| 8,715,620 B2 | 5/2014 | Sanders |
| 8,748,151 B2 | 6/2014 | Frevert |
| 9,080,220 B2 | 7/2015 | Auguet et al. |
| 9,107,815 B2 | 8/2015 | Hunt |
| 2002/0127247 A1 | 9/2002 | Steward et al. |
| 2003/0118598 A1 | 6/2003 | Hunt et al. |
| 2003/0138437 A1 | 7/2003 | Hunt |
| 2003/0215395 A1 | 11/2003 | Yu et al. |
| 2003/0215412 A1 | 11/2003 | Waugh |
| 2003/0236214 A1 | 12/2003 | Wolff et al. |
| 2004/0126396 A1 | 7/2004 | Aoki et al. |
| 2004/0220100 A1 | 11/2004 | Waugh et al. |
| 2004/0247614 A1 | 12/2004 | Dorr et al. |
| 2004/0247623 A1 | 12/2004 | Cady |
| 2005/0196414 A1* | 9/2005 | Dake ............... A61K 8/64 424/239.1 |
| 2006/0115480 A1 | 6/2006 | Hillman et al. |
| 2007/0267011 A1 | 11/2007 | Deem et al. |
| 2008/0200373 A1 | 8/2008 | Waugh et al. |
| 2009/0104234 A1 | 4/2009 | Francis et al. |
| 2009/0142430 A1 | 6/2009 | Sanders |
| 2009/0324647 A1 | 12/2009 | Borodic |
| 2010/0168023 A1* | 7/2010 | Ruegg ............... A61K 8/64 514/8.9 |
| 2011/0054442 A1 | 3/2011 | Sanders |
| 2011/0268765 A1 | 11/2011 | Ruegg et al. |
| 2012/0156244 A1 | 6/2012 | Horn |
| 2012/0251576 A1 | 10/2012 | Sanders |
| 2012/0263781 A1 | 10/2012 | Chancellor et al. |

FOREIGN PATENT DOCUMENTS

| | | |
|---|---|---|
| EP | 1112082 | 3/2010 |
| EP | 1776137 | 11/2014 |
| EP | 1778279 | 12/2014 |
| GB | 2418358 | 3/2006 |
| WO | WO 1995/28171 | 10/1995 |
| WO | WO 2000/015245 | 3/2000 |
| WO | WO 00/24419 | 5/2000 |
| WO | WO 2000/34308 | 6/2000 |
| WO | WO 2002/07773 | 1/2002 |
| WO | WO 2002/065986 | 8/2002 |
| WO | WO 2002/067917 | 9/2002 |
| WO | WO 2003/072049 | 9/2003 |
| WO | WO 2004/006954 | 1/2004 |
| WO | WO 2004/048519 | 6/2004 |
| WO | WO 2005/084361 | 9/2005 |
| WO | WO 2005/084410 | 9/2005 |
| WO | WO 2005/120546 | 12/2005 |
| WO | WO 2006/094193 | 9/2006 |
| WO | WO 2006/094263 | 9/2006 |
| WO | WO 2006/105450 | 10/2006 |
| WO | WO 2007/059528 | 11/2007 |
| WO | WO 2008/000490 | 1/2008 |
| WO | WO 2008/082885 | 7/2008 |
| WO | WO 2008/082889 | 7/2008 |
| WO | WO 2009/105369 | * 8/2009 |
| WO | WO 2010/078242 | 7/2010 |
| WO | WO 2011/057301 | 5/2011 |
| WO | WO 2011/084507 | 7/2011 |
| WO | WO 2011/160826 | 12/2011 |
| WO | WO 2012/019204 | 2/2012 |

OTHER PUBLICATIONS

Blitzer et al., "Botulinum toxin: basic science and clinical uses in otolaryngology," Laryngoscope (2001), 111(2), 218-226.

Braun et al., "Septal injection of botulinum neurotoxin A for idiopathic rhinitis: a pilot study," American journal of otolaryngology, (Jan.-Feb. 2012) vol. 33, No. 1, pp. 64-67.

Bushara, "Botulinum Toxin and Rhinorrhea", Otolaryngol Head Neck Surg., Mar. 1996 vol. 114 No. 3, p. 507.

Cheng et al., "Effect of a Purification on the Bioavailability of Botulinum Neurotoxin Type A," Foodborne Contaminants Research Unit, Food Research Institute, Comparative Pathology Lab, pp. 1-32, Jan. 2008.

Console et al., "Antennapedia and HIV Transactivator of Transcription (TAT) "Protein Transduction Domains" Promote Endocytosis of High Molecular Weight Cargo Upon Binding to Cell Surface Glycosaminoglycans", J. of Biological Chemistry, vol. 278, No. 37, Sep. 2003, pp. 35109-35114.

Fawell et al., "TAT-Mediated Delivery of Heterologous Proteins into Cells," Proc. Natl. Acad. Sci. vol. 91, pp. 664-668, 1994.

Futaki, "Intracellular Delivery of Biopolymers Using Membrane-Permeable Peptides," Membrane, 28(2), pp. 55-60, 2003.

Green, M. "Mutational analysis of HIV-1 TAT minimal domain peptides: identification of trans-dominant mutants that suppress HIV-LTR-driven gene expression", Cell, 58:215-223, 1989.

Gunes et al., "Evaluation of the effect of intranasal infiltrated botulinum toxin-A on a model of allergic rhinitis in rabbits: An Experimental Study," International Journal of Pediatric Otorhinolaryngology, 83, pp. 51-56, 2016.

Henriques. et al., "Cell Penetrating Peptides and Antimicrobial Peptides: How Different Are they?" Biochem. J., 399, pp. 1-7, 2006.

Jost, "Other indications of botulinum toxin therapy," European journal of neurology : the official journal of the European Federation of Neurological Societies, (Feb. 2006) vol. 13 Suppl 1, pp. 65-69.

Jung et al., "Biological Activity of Tat (47-58) Peptide on Human Pathogenic Fungi," Biochemical and Biophysical Research Communications, 345, pp. 222-228. 2006.

Jung et al., "Effective Antibacterial Action of Tat (47-58) by Increased Uptake into Bacterial Cells in the Presence of Trypsin," J. Microbiol. Biotechnol., 18(5), pp. 990-996, 2008.

Kalderon et al., "A Short Amino Acid Sequence Able to Specify Nuclear Location," Cell, vol. 39, pp. 499-509, 1984.

Keir, "Botulinum toxin-physiology and applications in head and neck disorders," Head & neck, (Jun. 2005) vol. 27, No. 6, pp. 525-535.

Kim et al., "The Effect of Botulinum Toxin Type A Injection for Intrinsic Rhinitis," The Journal of Laryngology and Otology, vol. 112, pp. 248-251, Mar. 1998.

Laing et al., "Botulinum toxin for treatment of glandular hypersecretory disorders," Journal of plastic, reconstructive & aesthetic surgery JPRAS, (Sep. 2008), vol. 61, No. 9, pp. 1024-1028.

Laskawi Rainer, "The use of botulinum toxin in head and face medicine: an interdisciplinary field," Head & face medicine, (2008) vol. 4, pp. 5.

Madison, K. "Barrier Function of the Skin: 'La Raison d'Être' of the Epidermis" Journal of Investigative Dermatology, 2003, 121, 231-241.

(56) References Cited

OTHER PUBLICATIONS

Mastrolorenzo et al., "Botulinus toxin, tetanus toxin, and anthrax lethal factor inhibitors," Drug Design of Zinc-Enzyme Inhibitors (2009), 705-720.
Moore, "Expanding clinical uses of botulinum neurotoxins," Treatments from Toxins 2007, 163-194.
Nagahara et al., "Transduction of Full-Length TAT Fusion Proteins into Mammalian Cells: TAT-p27kip1 Induces Cell Migration," Nature Medicine, vol. 1, No. 12, pp. 1449-1452, 1998.
Nigam et al., "Botulinum Toxin," Indian J. Dermatol, 55(1), pp. 8-14, 2010.
Abstract only, Nowak, "Application of botulinum toxin A in chronic intrinsic rhinitis," Otolaryngol Pol 2011; 65 (2): 103-105.
Ozcan et al., "The Effect of Intranasal Injection of Botulinum Toxin A on the Symptons of Vasomotor Rhinitis," American Journal of Otolaryngology—Head and Neck Medicine and Surgery, 27, pp. 314-318, 2006.
Park et al., "Mutational Analysis of a Human Immunodeficiency Virus Type 1 TAT Protein Transduction Domain Which is Required for Delivery of a Exogenous Protein into Mammalian Cells," Journal of General Virology, 83, pp. 1173-1181, 2002.
Persaud, et al. "An evidence-based review of botulinum toxin (Botox) applications in non-cosmetic head and neck conditions" Journal of the Royal Society of Medicine Short Report, 2013, 4:1-10.
Pharmalicensing, Ltd., "AIDS, Use of HIV-1 TAT, to Target and/or Activate Antigen-Presenting Cells, and/or to Deliver Cargo Molecules," from http://pharmalicensing.com/public/outlicensing/view/3766, 2001, 3 pages.
Pirtosek, "Botulinum toxin: other autonomic indication," European Journal of Neurology, (Sep. 2010) vol. 17, No. Suppl. 3, Sp. Iss.SI, pp. 637, FW 9-3.
Rohrbach, et al., "Botulinum toxin type A induces apoptosis in nasal glands of guinea pigs," Ann Otol Rhino! Laryngol., 2001, 110(11):1045-50.
Rohrbach, et al., "Minimally invasive application of botulinum toxin type A in nasal hypersecretion," ORL, 2001, 63(6):382-384.
Rohrbach et al., "Minimally invasive application of botulinum toxin A in patients with idiopathic rhinitis," Head & Face Medicine, 2009, 5:18, pp. 1-7.
Sapci, et al., "Investigation of the effects of intranasal botulinum toxin type A and ipratropium bromide nasal spray on nasal hypersecretion in idiopathic rhinitis without eosinophilia" Rhinology, 2008, 46(1):45-51.
Schwartz et al., Peptide-Mediated Cellular Delivery, Curr. Opin. Mol. Ther., vol./Iss: 2(2), pp. 162-167, 2000.
Shaari et al., "Rhinorrhea is Decreased in Dogs after Nasal Application of Botulinum Toxin," Otolaryngol Head Neck Surg, 112, pp. 566-571, 1995.
Simpson, "Identification of the Major Steps in Botulinum Toxin Action," Annu. Rev. Pharmacol. Toxico., 44, pp. 167-193, 2004.
Thant et al., "Emerging therapeutic applications of botulinum toxin," Medical Science Monitor (2003), 9(2), RA40-RA48.
Umezawa et al., "Development of β-peptides Having Ability to Penetrate Cell Membrane," 27[P1]I-133, Faculty of Pharmaceutical Sciences, Nagoya City University, 123(2), p. 29, Mar. 2003.
Unal, et al., "Effect of botulinum toxin type A on nasal symptoms in patients with allergic rhinitis: a double-blind, placebo-controlled clinical trial", Acta Otolaryngol 2003, 123(9):1060-1063.
Unal, "Investigate the effect of botulinum toxin type A (BTX-A) on nasal symptoms in patients with allergic rhinitis," Acta Oto-laryngologica, 2005, 125(2):223, Reply to letter to the editor.
Vivès et al., "A Truncated HIV-1 Tat Protein Basic Domain Rapidly Translocates Through the Plasma Membrane and Accumulates in the Cell Nucleus," J. Biol. Chem., 272(25), pp. 16010-16017, Jun. 1997.
Voet et al., Biochemistry, 2d ed., John Wiley and Sons, Inc., pp. 1275-1276, 1995.

Wang, et al., "The influence of botulinum toxin type A on vasomotor rhinitis and morphological study," Lin Chuang Er Bi Yan Hou Ke Za Zhi, 2003, 17(11):643-5.
Wen et al., "Experimental studies for botulinum toxin type A on allergic rhinitis in the rat," Zhonghua er bi yan hou ke za zhi, (Feb. 2004) vol. 39, No. 2, pp. 97-101.
Wen et al., "Inhibition of rhinorhea with botulinum toxin type A and the expression of VIP on nasal mucosa in allergic rhinitis rat," Disi Junyi Daxue Xuebao (2003), 24(19), 1769-1773.
Wen et al., "Botulinum Toxin Therapy in the Ovalbumin-Sensitized Rat," Neuroimmunomodulation, 14, pp. 78-83, 2007.
Wender et al., "The Design, Synthesis, and Evaluation of Molecules that Enable or Enhance Cellular Uptake: Peptoid Molecular Transporters," PNAS, 97(24), pp. 13003-13008, Nov. 21, 2000.
Wollina et al., "Botulinum toxin in dermatology—beyond wrinkles and sweat," Journal of cosmetic dermatology, (Dec. 2005) vol. 4, No. 4, pp. 223-227.
Yang, et al., "A comparison of the effects of botulinum toxin A and steroid injection on nasal allergy," Otolaryngol Head Neck Surg, 2008, 139(3):367-371.
Zhao et al., "Intracellular Cargo Delivery Using Tat Peptide and Derivatives," Medicinal Research Reviews, 24(1), pp. 1-12, 2004.
"Absorption and Distribution of Drugs," Rang and Dales's Pharmacology, Chapter 7,pp. 98-112, 2007.
Acquadro, M., et al., Treatment of Myofascial Pain with Butolinum Toxin A Toxin, Anesthesiology, 80(3):705-706, 1994.
Amann, R., et al., Intraplantar injection of nerve growth factor into the rat hind paw: local edema and effects on the termal nocieptive threshold, Pain 1995; 64:323-329.
Ashikaga, T., et al., Multiple daily insulin injections •in the treatment of diabetic retinopathy, The Job Study Revisited, Diabetes; 27(5):592-6; 1978.
Bischoff, S.C., et al., Effect of Nerve Growth Factor on the Release of Inflammatory Mediators by Mature Human Basophils, Blood; 79(10):2663-2669, 1992.
Borodic, G., et al., Immunoglobulin deposition in localized conjunctival amyloidosis, Am J Ophthalmol., 98 (5):617-622, 1984.
Borodic, G., et al., Pharmacology and histology of the therapeutic application of botulinum toxin, Chapter 10, pp. 119-157, Therapy with Botulinum Toxin (1984).
Borodic, G., et al., Peripapillary subretinal neovascularization and serous macular detachment, Association with congenital optic nerve pits, Arch Ophthalmol., 102(2):229-231, 1984.
Borodic, G., et al. Blepharospasm and its treatment, with emphasis on the use of botulinum toxin, Plast Reconstr Surg., 83(3): 546-54, 1989.
Borodic, G., et al., Dermis fat graft in eviscerated sockets, Ophthal Plast Reconstr Surg., 5(2):144-149, 1989.
Borodic, G., et al., Botulinum A toxin for the treatment of spasmodic torticollis dysphagia and regional toxin spread, Head & Neck, 12(5):392-399, 1990.
Borodic, G., et al., Botulinum A toxin for the treatment of adult-onset spasmodic torticollis, Plast Recnstr Surg., 87 (2):285-289, 1990.
Borodic, G., et al., Innervation zone of orbicularis oculi muscle and implications for botulinum A toxin therapy, Ophthal Plast Recostr Surg., 7(1) 54-60, 1991.
Borodic, G., et al., Contralateral injections of botuiinum A toxin for the treatment of hemifacial spasm to achieve increased facial symmetry, Plast Reconstr Surg., 90(6):972-977, 1992.
Borodic, G., et al., Effects of repeated botulinum toxin injections on orbicularis oculi muscle, J Clin Neuroophthalmol., 12(2):121-127, 1992.
Borodic, G., et al., Botulinum A toxin for spasmodic torticollis: multiple vs single injection points per muscle, Head & Neck, 14(1):33-37, 1992.
Borodic, G., Botulinum A toxin for (expressionistic) ptosis overcorrection after frontalis sling, Ophthalmic Plast Recostr Surg., 8(2):137-42, 1992.
Borodic, G., et al., Treatment of spasticity with botulinum toxin, American Neural., 31(1):113, 1992.

(56) References Cited

OTHER PUBLICATIONS

Borodic, G., et al., Botulinum A Toxin for treatment of aberrant facial nerve regeneration, Plast Reconstr Surg., 91(6):1042-1045, 1993.
Borodic, G., et al., Botulinum B toxin as an alternative to botulinum A toxin: a histologic study, Ophthal Plast Recostr Surg. 9(3):182-190, 1993.
Borodic, G., et al., Therapeutic botulinum toxin: histologic effects and diffusion properties, DasGupta BR, ed, Botulinum and Tetanus Neurotoxins. Plenum Press, New York, pp. 623-645, 1993.
Borodic, et al., Antibodies to Botulinum Toxin, Opthalmology, vol. 101, No. 7, p. 1158, Jul. 1994.
Borodic, G., et al., New concepts in botulinum toxin therapy, Drug Safety, 11(3): 145-152, 1994.
Borodic, G., et al., Histologic assessment of dose-related diffusion and muscle fiber response after therapeutic botulinum A toxin injections, Movement Disorders; 9(1):31-39, 1994.
Borodic, G., Therapeutic botulinum toxin, The Lancet, 344(8933):1370, 1994.
Borodic et al., Antibodies to Botulinum Toxin, Neurology, p. 304, 1995.
Borodic et al., Botulinum Toxin Therapy, Immunologic Resistance, and Problems with Available Materials, Neurology, 46, pp. 26-29, 1996.
Borodic, G., et al., Photophobia and benign essential blepharospasm, American Society of Ophthalmic Plastic and Reconstructive Surgery, p. 35, 1996.
Borodic, G., Myasthenic crisis after butolinum toxin, The Lancet; 352, p. 1832, 1998.
Borodic, G., Botulinum toxin: issues and applications, Curr. opin. Otolaryngology Head & Neck Surgery, 7:219-225, 1999.
Bottinger, H., et al., Inhibition of histamine release from rat mast cells by botulinum C2 toxin, Int Arch Allergy Appl Immunol., 84(4):380-384, 1987.
Brooks, A., et al., Reactive oxygen species generation and histamine release by activated mast cells: modulation by nitric oxide synthase inhibition, Br J Pharmacol., 128:585-590, 1999.
Bushara et al., "Botulinum Toxin and Sweating," J. Neurol. Neurosurg., Pyshctr., 57(11), pp. 1437-1438, 1994.
Buzzi, M.G., et al., 5-Hydroxytryptamine receptor agonists for the abortive treatment of vascular headaches block mast cell, endothelial and platelet activation within the rat dura mater after trigeminal stimulation, Brain Res., Jun. 26; 583(1-2):137-49, 1992 (Abstract only).
Buzzi, M.G., et al., Neurogenic model of migraine, Cephalalgia, 15(4):277-80, 1995 (Abstract only).
Calderone, J., et al., Intraocular pathology of trisomy 18 (Edwards' syndrome): report of a case and review of the literature, Br J Ophthalmol., 67(3): 162-169, 1983.
Chen et al., "Botulinum toxin type A decreases the concentration of acetylcholinesterase in nasal glands of guinea pig," Lin chuang er bi yan hou ke za zhi = Journal of clinical otorhinolaryngology, vol. 19, No. 8, pp. 370-372, 2005.
Chen, X., et al., NOS Inhibitor antagonism of PGE2-induced mechanical sensitization of cutaneous C-fiber nociceptors in the rat, Am Psych Soc., pp. 963-966, 1999.
Coderre, T., et al., Neural control of vascular permeability: interactions between primary afferents, mast cells, and sympathetic efferents, Journal of Neurophysiology, vol. 62, No. 1, pp. 48-58, Jul. 1989.
Dimitradou, V., et al., Trigeminal sensory fiber stimulation induces morphological changes reflecting secretion in rat dura mater mast cells, Neuroscience , 44(1):97-112, 1991.
Dimitriadou, V., et al., Ultrastructural evidence for neurogenically mediated changes in blood vessels of the rat dura mater and tongue following antidromic trigeminal stimulation, Neuroscience, 48(1):187-203, 1992.
Dines, K., et al., Mast cell interactions with the nervous system: relationship to mechanisms of disease, J Neuropathol Exp Neural., 56(6):627-640, 1997.
First, E., et al., Does standardization of botulinum toxin, The Lancet, 343(8904):1035, 1994.
Fujishima, H., et al., Elevated levels of substance Pin tears of patients with allergic coniunctivitis and vernal keratoconjunctivitis, Clin Exp Allergy, 27:372-378, 1997.
Gizurarson, S. "Anatomical and Histological Factors Affecting Intranasal Drug and Vaccine Delivery", Current Drug Delivery, 9:566-582, 2012.
Hagiwara et al., "Deimination of Arginine Residues in Nucleophosmin/B23 and Histones in HL-60 Granulocytes," Biochem. Biophys. Res. Commun., 290(3): 979-983, 2002.
Hayashi, N., et al., Giant cell angiofibroma of the orbit and eyelid, Ophthalmology, 106(6):1223-1229, 1999.
Inagaki et al., "$Ca^{2+}$-dependent Deimination-induced Disassembly of Intermediate Filaments Involves Specific Modification of the Amino-terminal Head Domain," J. Biol. Chem., 264(30): 18119-18127, 1989.
Jankovic et al., "Therapeutic Uses of Botulinum Toxin," NEJM, 324, pp. 1186-1994, 1991.
Jasmin, L., CNS induced neurogenic cystitis is associated with bladder mast cell degranulation in the rat, American Urological Association, Inc., vol. 164, pp. 852-855, Sep. 2000.
Jensen, W., et al., The susceptibility of the mallard duck (*Anas platyrhynchos*) to Clostridium botulinum $C_2$ toxin, Japan J Med Sci Biol., 33(2):81-86, 1980.
Junghans, "Botulinum toxin type A as a possible therapeutic option in the treatment of allergic and idiopathic rhinitis—results of a randomized, double-blind, placebo-controlled study," Avail.: Metadata on Internet Documents, Order No. 405822 From: Metadata Internet Doc. [Ger. Diss.] 2010, (D0716-4), URL: http://www.meind.de/search.py?recid=405822, pp. 1-225 (English summary).
Just, I., et al., ADP-ribosylation of *Drosophila* indirect-flight-muscle actin and arthrin by Clostridium botulinum C2 toxin and Clostridium perfringens iota toxin, Biochem J., 291 (Pt 2):409-412, 1993.
Kellogg, D.L., et al., Cutaneous active vasodilation in humans in mediated by cholinergic nerve cotransmission, Gire Res., 776(6)1222-8, 1995 (Abstract only).
Kinde, H., et al., Clostridium botulinum type-C intoxication associated with consumption of processed alfalfa hay cubes in horses, J Am Vet Med Assoc., 199(6), pp. 742-746, 1991.
Kokumai, S., et al., Effect of capsaicin as a neuropeptide-releasing substance on sneezing reflex in a type I allergic animal model, Int Arch Allergy Immunol., 98(3):,256-61, 1992 (Abstract only).
Lambiase, A., et al., Increase plasma levels of substance P in Vernal Keratoconjunctivitis, Invest Opthalmol Vis Sci., 38:2161-2164, 1997.
Lambiase, A., et al., Expression of nerve growth factor receptors on the ocular surface in healthy subjects and during manifestation of inflammatory diseases, IOVS, 39(7): 1272-1725, 1998.
Lassen, L.H., et al., Histamine induces migraine via the H1-receptor. Support for the NO hypothesis of migraine, Neuroreport, 6(11):1475-9, 1995 (Abstract only).
Leon, A., et al., Mast cells synthesis, store, and release nerve growth factor, Proc Natl Acad Sci., 91 3739-3743, 1994.
Levi-Montalcini, R, et al., Update of the NGF saga, J Neurol Sci., 130:119-127, 1995.
Levi-Montalcini, R., et al., Nerve growth factor: from neurotrophin to neurokine, TINS, 19(11):514-520, 1996.
Levine, J.D., et al., Intraneuronal substance P contributes to the severity of experimental arthritis, Science, No. 2; 226(4674):547-549, 1984 (Abstract only).
Lewin, G., et al., Nerve Growth Factor and Nociception, TINS, 16(9):353-359, 1993.
Matter, K., et al., Actin involvement in exocytosis from PC12 cells: studies on the influence of botulinum C2 toxin on stimulated noradreneline release, J Neurochem, 52(2):370-376, 1989.
Mauss, S., et al., Inhibition of the contraction of the isolated longitudinal muscle of the guinea-pig ileum by botulinum C2 toxin: evidence for a role of G/F-actin transition in smooth muscle contraction, Naunyn Schmiedebergs Arch Pharmacol, 340(3):345-351, 1989.

(56) References Cited

OTHER PUBLICATIONS

Meijer, F., et al., Nitric oxide plays a role as mediator of conjunctival edema in experimental allergic conjunctivitis, Exp Eye Res., 62(4):359-65, 1996 (Abstract only).

Mendell, L., et al., Neurotrophins, nociceptors, and pain, Microscopy Res Technique, 45:252-261, 1999.

Merayo-Lloves et al., Experimental Model of Allergic Conjunctivitis to Ragweed in Guinea Pig, Curr. Eye Research, 14, pp. 487-494, 1995.

Mio, M , et al., Substance P-induced histamine release from rat peritoneal mast cells and its inhibition by antiallergic agents and calmodulin inhibitors, Immunopharmacology, 22, pp. 59-66, 1991.

Monteforte, R., et al., Morphological changes in frog mast cells induced by nerve stimulation in two, Neuroscience Letters 315, pp. 77-80, 2001.

Moskowitz, M.A., et al., Neuroeffector functions of sensory fibres: implications for headache mechanisms and drug actions, J Neurol., 238 Suppl 1:S18-22, 1991.

Nakamura, S., et al., Sporulation and $C_2$ toxin production by Clostridium botulinum trype C strains producing no $C_1$ toxin, Microbial Immunol., 22(10): 591-596, 1978.

Nakamura, S., et al., $C_2$ toxin production by Clostridium botulinum type C strains producing no $C_1$ toxin, Jpn J Med Sci Biol., 32(2):128-129, 1979.

Nowak et al., "Application of botulinum toxin A in chronic intrinsic rhnitis," Otolaryngol. Pol, 65 (2), pp. 103-105 2011.

Ohishi, I, et al., Histopathological effect of botulinum C2 toxin on mouse intestines, Infect Immun., 43(1):54-58, 1984.

Pardo, F., et al., Long-term follow-up of patients undergoing definitive radiation therapy of sebaceous carcinoma of the ocular adnexae, Int J Radial Oncol Biol Phys., 4(5):1189-1190, 1996.

Pasricha et al., "Intrasphincteric Botulinum Toxin for the Treatment of Achalasia," NEJM, 332, pp. 774-778, 1995.

Pearce, L., et al., Botulinum Toxin: death versus localize denervation, JR Soc Med., 88(4):239-40, 1995.

Pearce, L., et al., Pharmacologic characterization of botulinum toxin for basic science and medicine, Toxicon, 35 (9):1373-1412, 1997.

Pearce, L., et al., The median paralysis unit: a more pharmacologically relevant unit of biologic activity of botulinum toxin, Toxicon, 33(2):217-227, 1995.

Pearce, L., et al., Measurement of botulinum toxin activity: evaluation of the lethality assay, Toxicol. Appl. Pharmacol., 128(1):69-77, 1994.

Pearce, L., et al., Botulinum toxin potency: a mystery resolved by the median paralysis, JR Soc Med., 87(9):571-572, 1994.

Pedrosa, C.A., et al., Determinants and impact of headache after acoustic neuroma surgery, The American Journal of Otology, vol. 15, No. 6, pp. 793-797, Nov. 1994.

Ritter, A., et al., Regulation of myelinated nociceptor function by nerve growth factor in neonatal and adult rats, Br Res Bui., 30:245-249, 1993.

Sanico, A., et al., Nerve growth factor expression and release in allergic inflammatory disease of the upper airways, Am J Respir Crit Care Med., 161:1631-1635, 2000.

Schellekens et al., "Citrulline is an Essential Constituent of Antigenic Determinants Recognized by Rheumatoid Arthritis-specific Autoantibodies," J. Clin. Invest., 101(1): 273-281, 1998.

Scholzen, et al., Exp. Dermatol., 7, pp. 81-96, 1998.

Simpson, L., A comparison of the pharmacological properties of Clostridium botulinum type $C_1$ and $C_2$ toxins, J Pharmacol Exp Ther., 223(3):695-701, 1982.

Simpson, L., Molecular basis for the pharmacological actions of Clostridium botulinum type $C_2$ toxin, J Pharmacol Exp Ther., 230(3):665-669, 1984.

Soter, N.A., et al., Release of mast-cell mediators and alterations in lung function in patients with cholinergic urticaria, N Engl J Med, 302(11):604-8, Mar. 13, 1980 (Abstract only).

Takeda, N., et al., Neurogenic inflammation in nasal allergy; histochemical and pharmacological studies in guinea pigs. A review, Acta Otolaryngol Suppl., 501:21-4, 1993 (Abstract only).

Tarsy, D., et al., Myasthenia gravis after botulinum Toxin A for Meige syndrome, Movement Disord., 15(4):736-738, 2000.

The Merck Manual, 16th ed., Barkow, ed., pp. 318-320, 1308-1311, 1992.

Tranquill et al., "Enhanced T Cell Responsiveness to Citrulline-containing Myelin Basic Protein in Multiple Sclerosis Patients," Multiple Sclerosis, 6(4): 220-225, 2000.

Travell, J.G., et al., Myofascial Pain and Dysfunction the Trigger Point Manual, The Upper Extremities, Background and Principles, Chapter 2, pp. 29, 32-33, 1992.

Troll, G., et al., Diplopia after cataract surgery using 4% lidocaine in the absence of Wydase, J Clin Anesth., 11 (7):615-616, 1999.

Wang, Z.Y., et al., The contribution of nitric oxide to endotoxin-induced ocular inflammation: interaction with sensory nerve fibres, Br J Pharma col., 118(6):153-43, 1996 (Abstract only).

Wex, C., et al., Effects of clostridium botulinum C2-induced depolymerisation of actin on degranulation of suspended and attached mast cells, Nauny-Schmiedeberg's Arch Pharmacol., 355:319-327, 1997.

Wollina, et al., Adjuvant Botulinum Toxin A in Dyshidrotic Hand Eczema: a controlled Prospective Pilot Study without left-right Comparison, J. Eur. Acad. Derm. Venerol. 2002;16:40-42.

Woolf, C., et al., Peripheral cell types contributing to the hyperalgesic action of nerve growth factor in inflammation, J Neurosc., 16(8): 2716-2723, 1996.

Veien, et al., Treatment of Hand Eczema, Skin Terapy Lett. 2003;8(5):4-7.

Yamaji, M., et al., Role of substance Pin experimental allergic conjunctivitis in guinea pigs, Meth Find Exp Clin Pharmaco., 19(9):637-643, 1997.

* cited by examiner

COMPOSITIONS AND METHODS FOR SAFE TREATMENT OF RHINITIS

FIELD OF THE INVENTION

This invention relates to compositions and methods for treating rhinitis using topical *botulinum* toxin compositions. More particularly, the invention relates to treating the symptoms of rhinitis using intranasal administration of topical *botulinum* toxin compositions that contain a purified *botulinum* neurotoxin.

BACKGROUND OF THE INVENTION

Rhinitis is a worldwide health problem associated with nasal inflammation and characterized by symptoms of congestion, rhinorrhea, sneezing and itching. Allergic rhinitis is the most common form of rhinitis and affects up to 30% of adults and 40% of children in the United States. Symptoms of both allergic as well as non-allergic types of rhinitis can significantly impair patients' quality of life. Moreover, allergic rhinitis often coexists with other atopic conditions, such as asthma, sinusitis and sleep apnea. Rhinitis is induced by overstimulation of parasympathetic innervation of the nasal mucosal tissue via release of acetylcholine and inflammatory mediators such as vasoactive intestinal peptide (VIP). Pharmacologic therapy (e.g., anti-histamines, decongestants, corticosteroids, anti-cholinergics, etc.) and in the case of allergic rhinitis, allergic immunotherapy, require either frequent (one or more times per day) administration often with side effects or a long-term process of desensitization with limited effectiveness for many patients.

*Botulinum* toxin type A is obtained from serotype A of *Clostridium botulinum*. *Botulinum* toxin type A acts to block the release of acetycholine from the presynaptic nerve terminal with consequent induction of muscular paralysis. Based on this anti-cholinergic activity, *botulinum* toxin type A has been used widely in the treatment of muscle spasticity disorders, and for the cosmetic treatment of frown lines and wrinkles. In addition to these applications in the neuromuscular system, *botulinum* toxin type A blocks parasympathetic cholinergic transmission and has been used for treatment of glandular hypersecretory disorders, such as hyperhidrosis, Frey's syndrome, sialorrhea, epiphora, rhinorrhea, and sialadenitis. It has also been shown that *botulinum* toxin type A can be used to suppress electrically stimulated rhinorrhea in a dog model, which is consistent with recent reports demonstrating the effect of muscarinic cholinergic agents on canine nasal veins. Subsequent studies in animal models and in human patients with different types of rhinitis demonstrated that local application of *botulinum* toxin type A effectively reduced rhinitis symptoms. In humans, one *botulinum* toxin type A treatment injected directly into the nasal turbinates significantly reduced rhinorrhoea for four weeks (Kim K S, Kim S S, Yoon J H et al. The effect of *botulinum* toxin type A injection for intrinsic rhinitis. *J Laryngol Otol.* 112:248-51, 1998) to eight weeks (Unal M, Sevim S, Doğu O et al. Effect of *botulinum* toxin type A on nasal symptoms in patients with allergic rhinitis: a double-blind, placebo-controlled clinical trial. *Acta Otolaryngol.* 123:1060-3, 2003), and provided better symptom relief than corticosteroid therapy for 20 weeks (Yang T Y, Jung Y G, Kim Y H et al. A comparison of the effects of *botulinum* toxin A and steroid injection on nasal allergy. *Otolaryngol Head Neck Surg.* 139:367-71, 2008). In addition, treatment of rhinitis using clostridial neurotoxins has been reported in U.S. Pat. Nos. 5,766,605; 7,494,661; 7,879,340; 8,088,360; and 8,088,361, as well as in U.S. Pre-Grant Publication Nos: 20120071395, 20110150975, 20110091505, 20110091504, 20110086072, 20110054442, 20060153876, 20060008462, and 20040248188. Some of these references report delivering topical liquid formulations containing commercially available *botulinum* type A complexes by saturating a sponge or gauze packing with a topical *botulinum* toxin formulation and inserting the sponge or gauze packing into the nasal cavity. The practical difficulties associated with this methodology raises certain procedural issues as well as safety concerns. In addition to the treatment of rhinitis, clostridial neurotoxins have been used in the treatment of sinusitis (see, e.g. U.S. Pat. No. 8,092,781, WO2011/084507). These and all other references cited herein are hereby incorporated by reference in their entirety.

Despite this early evidence of efficacy, the use of *botulinum* toxin type A for treating rhinitis has not been widely accepted among clinicians and patients. One reason for this is the oral toxicity of commercially available *botulinum* toxin formulations. *Botulinum* toxin type A, in its native form, exists as part of a protein complex that is produced by *C. botulinum* bacteria. The native protein complex contains, in addition to the *botulinum* toxin type A neurotoxin molecule, stabilizing hemaglutinin and non-hemaglutinin proteins (sometimes referred to as "accessory proteins") which are capable of protecting the *botulinum* neurotoxin molecule from degradation in the harsh acidic environment of the stomach. Currently available commercial *botulinum* toxin type A formulations are made using native *botulinum* toxin protein complexes. Thus, in the event of accidental oral ingestion during the treatment of rhinitis, the accessory proteins will enable the *botulinum* toxin to be passed through the stomach to the small intestine, where it is absorbed into the bloodstream. If this occurs, systemic poisoning, paralysis, and even death result. Accordingly, treatment of rhinitis using the presently available commercial *botulinum* toxin formulations in topical preparations has been disfavored, even though *botulinum* toxin has been reported to be able to bind to mucosal epithelial cells and become trancytosed across mucosa. (See, e.g., U.S. Pat. No. 8,092,781).

While *botulinum* toxin has been reported to cross mucosa in the respiratory and gastrointestinal tract, *botulinum* toxin does not penetrate intact skin, owing to its size. See, e.g., S. Arnon et al., "*Botulinum* Toxin as a Biological Weapon—Medical and Public Health Management," JAMA, Vol. 285, No. 8, p. 1059 ff. Accordingly, unlike delivering *botulinum* toxin to mucosa, one must take special measures to either disrupt the skin (see, e.g., U.S. Pre-Grant Publication No. 20070088248) or to enhance penetration of *botulinum* toxin via use of a carrier (see, e.g., U.S. Pat. No. 7,807,780, and U.S. Pre-Grant Publication Nos. 20050196414, 20070077259) when administering *botulinum* toxin transdermally.

SUMMARY OF THE INVENTION

In one aspect, the invention relates to a method for treating rhinitis. The method involves intranasally administering a *botulinum* toxin composition to a patient in need of treatment for rhinitis. In certain embodiments, the *botulinum* toxin composition is a topical composition that includes (i) purified *botulinum* toxin neurotoxin (ii) at least one carrier, and (iii) at least one viscosity modifier. In such embodiments, the *botulinum* toxin is a 150 kDa *botulinum* neurotoxin type A which contains little or no toxin accessory proteins or human/animal-derived components. Also, the carrier comprises a positively charged backbone with positively charged efficiency groups covalently attached thereto, and the viscosity modifier is a preferably a poloxamer. Preferably, the carrier and viscosity modifier help to retain the intranasal composition at the site of administration and minimize the possibility of drainage or leakage to other sites, e.g. down the throat.

DETAILED DESCRIPTION OF THE INVENTION

Figure 1:
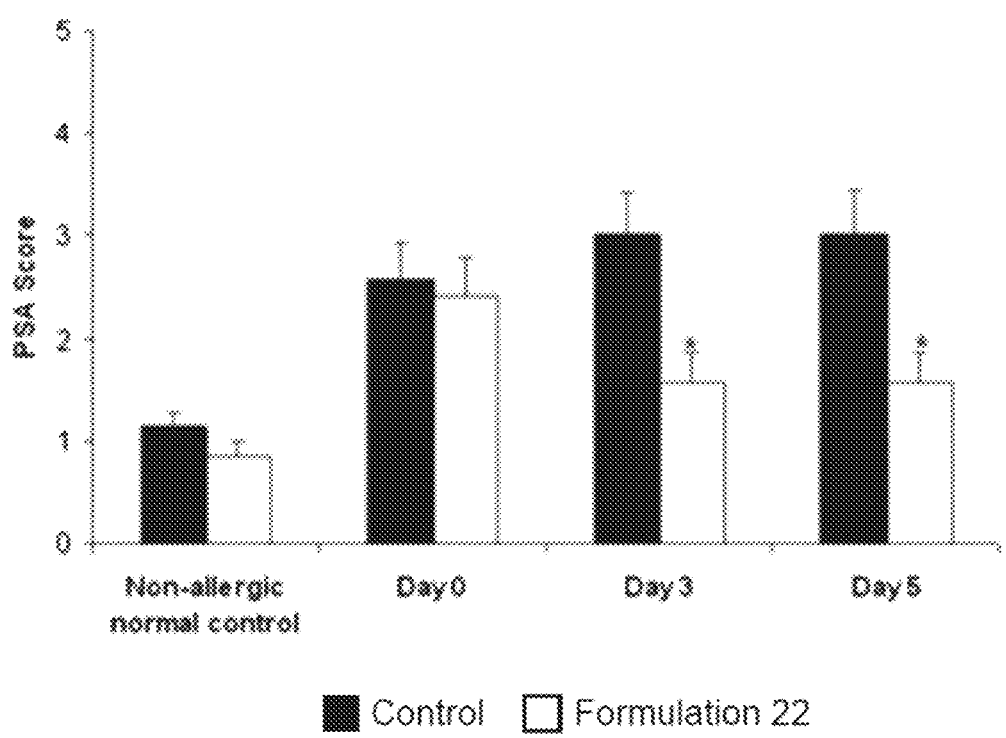
FIG. 1. Graph indicating performance severity assessment score (PSA) of rats (mean±SEM) on days 3, 5 and 7 after treatment with control (filled bars) or reconstituted Formulation 22 (open bars).

The present invention is based, at least in part, on the discovery that certain *botulinum* toxin compositions need not be administered by injection for the treatment of rhinitis. The *botulinum* toxin compositions according to the invention can be administered by intranasally applying a topical *botulinum* toxin formulation. It is believed that the present topical *botulinum* toxin compositions offer at least two advantages over the injectable *botulinum* toxin formulations in the prior art. First, the present compositions utilize purified *botulinum* neurotoxin that is substantially free of the accessory proteins, rather than *botulinum* toxin complexes as used in conventional injectable formulations. Without its native accessory proteins, *botulinum* neurotoxin is susceptible to degradation in a patient's gastrointestinal tract. Accordingly, the present topical *botulinum* toxin compositions are far less likely to cause systemic poisoning and death in the event that accidental oral ingestion occurs. In addition, the at least one carrier and at least one viscosity modifier help to prevent migration of the topical composition from the site of administration, thereby minimizing the possibility of migration and inadvertent oral ingestion. Without wishing to be limited by theory, it is believed that the carrier contributes to the localization of the *botulinum* toxin by facilitating transport of the toxin across the mucosa to its site of action and minimizing unwanted diffusion of the *botulinum* toxin away from the area in need of treatment. Moreover, it is believed that the viscosity modifier contributes to creating a formulation that essentially stays in the location where it is applied. Accordingly, the topical *botulinum* toxin compositions of the present invention provide an improved safety profile over the previous injectable *botulinum* toxin compositions.

The invention is suitable for the treatment of all forms of rhinitis, non-limiting examples of which include infectious rhinitis, vasomotor rhinitis, allergic rhinitis, rhinitis medicamentosa, atrophic rhinitis, rhinitis sicca, and polypous rhinitis. The compositions and methods disclosed herein can be used to treat rhinitis or characteristic symptoms of the same, e.g. nasal inflammation, nasal congestion, rhinorrhea, sneezing and/or itching. Thus, for example, the invention may be used to treat rhinitis-like symptoms, such as those that occur following certain ear-nose-throat (ENT) procedures, a non-limiting example of which is rhinoplasty. When the invention is being used to treat rhinitis, the rhinitis can be allergic rhinitis or non-allergic rhinitis, where the latter type of rhinitis can be either inflammatory or non-inflammatory rhinitis (e.g. vasomotor rhinitis). It is also contemplated that multiple forms of rhinitis can be treated simultaneously with the compositions and methods of the present invention. For example, the compositions and methods of the present invention can be used to treat a patient suffering from both allergic rhinitis and vasomotor rhinitis, a condition that is commonly referred to as "mixed rhinitis." The methods can also be used to treat rhinitis when it occurs in patients who have a condition in combination with other atopic conditions, such as asthma, sinusitis and sleep apnea.

Generally, the topical *botulinum* toxin compositions contemplated by the invention can be administered using an applicator that is inserted into a patients' nostril. Optionally, the topical administration may be achieved using visual guidance with the assistance of a nasal speculum and/or headlamp as necessary. The topical composition is applied with the applicator to inner surfaces of the nose, non-limiting examples of which include the surfaces of the inferior turbinate, middle turbinate and the superior turbinate. The topical *botulinum* toxin compositions may be administered via one nostril or via both nostrils, if deemed necessary. Application of the topical composition may be achieved, for example, by using a custom applicator, such as the one described in U.S. Pre-Grant Publication No. 2011010621 to Ruegg et al., which is hereby incorporated by reference in its entirety. Alternatively, the topical composition may be applied first to an implement, such as a swab, which is then used to spread the topical composition over the area in need of treatment.

After the topical *botulinum* toxin compositions of the invention are administered, they optionally may be allowed to remain in place for a certain dwell period in order to increase the amount of *botulinum* neurotoxin that is delivered to the nasal tissues in need of treatment. As will be appreciated by those of skill in the art, the specific dwell time that is selected will depend on factors such as the severity of the rhinitis, the desired amount of *botulinum* toxin to be delivered, the concentration of the *botulinum* neurotoxin in the topical *botulinum* toxin composition, the concentration of the carrier in the topical *botulinum* toxin composition, and the viscosity of the topical *botulinum* toxin composition. Optionally, the dwell times may range from 5 seconds to 60 minutes, 30 seconds to 45 minutes, 1 minute to 30 minutes, 5 minutes to 20 minutes or 10 minutes to 15 minutes. Optionally, the dwell time may be 10, 20, 30 40 or 50 minutes. After the chosen dwell time has elapsed, the excess topical *botulinum* toxin composition on the inner surfaces of the nose, to the extent that any such excess exists, may be removed by any suitable means, non-limiting examples of which including swabbing the inner surfaces of the nose or flushing the nostrils with a liquid, such as saline.

Purified *Botulinum* Toxin

The term "purified *botulinum* neurotoxin," as used herein, refers to any of the known types of purified *botulinum* neurotoxin, whether produced by the bacterium or by recombinant techniques, as well as any such types that may be subsequently discovered, including engineered variants or fusion proteins. For example, the purified *botulinum* neurotoxin may be a compound that has toxin activity but contains one or more chemical or functional alterations on any part or on any chain relative to naturally occurring or recombinant native neurotoxins. The purified *botulinum* neurotoxin may be a modified neurotoxin that has at least one of its amino acids deleted, modified or replaced, as compared to a native neurotoxin molecule while maintaining significant neurotoxin activity. In this regard, modified *botulinum* neurotoxins obtained from a native *botulinum* neurotoxin with one or more of its amino acids replaced by conservative substitutions are expressly contemplated by the invention. Alternatively, the purified *botulinum* neurotoxin may be one that has been modified in a way that, for instance, enhances its properties or decreases undesirable side effects, but that still retains the desired *botulinum* toxin activity. The purified *botulinum* neurotoxin may be prepared using recombinant or synthetic chemical techniques (e.g. a recombinant peptide, a fusion protein, or a hybrid neurotoxin, as prepared from subunits or domains of different *botulinum* toxin serotypes (see, e.g., U.S. Pat. No. 6,444,209, the contents of which are incorporated by reference in their entirety). The purified *botulinum* neurotoxin may also be a portion of the overall molecule that has been shown to possess the necessary *botulinum* toxin neurotoxin activity, and in such case may be used per se or as part of a combination or conjugate molecule, for instance a fusion protein. Additionally, the purified *botulinum* neurotoxin may be in the form of a purified *botulinum* neurotoxin precursor, which may itself be non-toxic, for instance a nontoxic zinc protease that becomes toxic on proteolytic cleavage.

Optionally, the purified *botulinum* neurotoxin is obtained by isolating it from *C. botulinum* bacteria. In this regard, the invention expressly contemplates the use of purified *botulinum* neurotoxins selected from the group of clostridial neurotoxins consisting of serotypes A, B, C1, D, E, F, G and combinations thereof. In the compositions of the present invention, the purified *botulinum* neurotoxin is present as an isolated *botulinum* neurotoxin (e.g., purified *botulinum* toxin type A protein) that is stabilized by exogenous stabilizers. Optionally, the compositions are substantially free of the accessory proteins normally found in native *botulinum* toxin complexes. Preferably, the *botulinum* neurotoxin is sufficiently free of accessory proteins that the neurotoxin is susceptible to degradation in the gastrointestinal tract if ingested. For example, *botulinum* neurotoxin may be substantially free of accessory proteins if at least 70%, 80%, 85%, 90%, 95%, 96%, 97%, 98%, 99%, 99.5% or 99.9% of the accessory proteins found in the native *botulinum* toxin complexes have been removed, with each of the ranges from these specifically enumerated lower limits to 100% being a distinct embodiment expressly contemplated by the invention. Optionally, the purified *botulinum* neurotoxin is entirely free of the neurotoxin-associated proteins characteristic of the 900 kDa *botulinum* toxin complex. Stabilized *botulinum* neurotoxin formulations containing such exogenous stabilizers have been reported, for example, in U.S. Pre-Grant Publication 20100330123 entitled "Albumin Free *Botulinum* Toxin Formulations," which is hereby incorporated by reference in its entirety.

The purified *botulinum* neurotoxins contemplated by the invention are less toxic with respect to oral ingestion than native *botulinum* toxin, owing to the removal of some or all of the accessory proteins normally accompanying the native *botulinum* neurotoxin. The invention contemplates removing a sufficient amount of the native accessory proteins to obtain a purified *botulinum* neurotoxin that is 10-fold, 20-fold, 30-fold, 40-fold, 50-fold, 60-fold, 70-fold, 80-fold or 90-fold less toxic with respect to oral ingestion than native *botulinum* toxin. For example, the purified *botulinum* neurotoxin may be 10-fold to 90-fold less toxic, 20-fold to 80-fold less toxic, 30-fold to 70-fold less toxic, or 40-fold to 60-fold less toxic with respect to oral ingestion. Optionally, the purified *botulinum* toxin may be 50-fold to 95-fold less toxic, 60-fold to 90-fold less toxic, or 70-fold to 85-fold less toxic with respect to oral ingestion than the native *botulinum* toxin. The relative toxicities of *botulinum* neurotoxin-containing formulations may be determined using test animal studies, as described herein. Removal of the accessory proteins may be accomplished using any methods known in the art, such as treating the native *botulinum* toxin complexes with red blood cells at a pH of 7.3, or by using separation methods such as chromatography (See, e.g., U.S. Pre-Grant Publication No. 20110092682, the contents of which are incorporated by reference in their entirety).

The purified *botulinum* neurotoxin is present in the topical *botulinum* toxin compositions of the invention in an effective amount to treat rhinitis. In this context, the term "effective amount" refers to an amount of purified *botulinum* neurotoxin that is sufficient to ameliorate one or more symptoms of rhinitis safely. For example, when the purified *botulinum* neurotoxin is serotype A, the amount of purified *botulinum* neurotoxin may range from 250 U/mL to 50,000 U/mL, 500 U/mL to 25,000 U/mL, 2,500 U/mL to 12,500 U/mL, or 5,000 U/mL to 10,000 U/mL. In general, effective amounts for the purified *botulinum* neurotoxins disclosed herein may range from 50 U/mL to 450,000 U/mL, preferably from 5,000 U/mL-400,000 U/mL, more preferably from 10,000 U/mL-150,000 U/mL, and even more preferably from 20,000 U/mL to 125,000 U/mL. Optionally, the effective amount of purified *botulinum* toxin may range from 20,000 U/mL to 40,000 U/mL, 45,000 U/mL to 95,000 U/mL, or 100,000 U/mL to 200,000 U/mL.

The invention also contemplates topical *botulinum* toxin compositions that contain purified botulinim neurotoxin present in the composition a concentration that ranges from about 5 ng/mL to about 50 ng/mL, such as, for example about 5 ng/mL, about 10 ng/mL, about 15 ng/mL, 20 ng/mL, about 25 ng/mL, about 30 ng/mL, about 35 ng/mL, about 40 ng/mL, about 45 ng/mL or about 50 ng/mL. Of course, the specific amount of purified *botulinum* neurotoxin in a given topical formulation will depend on the chosen carrier and viscosity modifier, and can be readily determined by a person of skill in the art. Optionally, the concentration and volume of the topical *botulinum* toxin composition is selected so as to provide a dose of *botulinum* toxin in the range of 1 ng to 50 ng, or 5 ng to 40 ng, or 10 ng to 30 ng, or 15 ng to 25 ng. For example, if desired, the dose of *botulinum* toxin can be in a range from 1 ng to 10 ng, 2 ng to 8 ng, or 3 ng to 6 ng. The dose of *botulinum* toxin optionally may be in the range of 0.5 ng to 5 ng, 1 ng to 5 ng, or 2 ng to 4 ng. The dose of *botulinum* toxin in certain preferred embodiments is 1, 2, 3, 4, or 5 ng. Optionally, the volume of the applied topical *botulinum* toxin composition is in the range of 0.02-0.5 mL, 0.05 to 0.4 m, 0.07 to 0.3 mL or 0.09 to 0.2 mL, and the concentration of the topical *botulinum* toxin is selected to provide a dose of 1 to 10 ng, or 1 to 5 ng.

Carriers

In addition to purified *botulinum* neurotoxin, the topical *botulinum* toxin compositions of the invention preferably contains a carrier to promote the transport of the purified *botulinum* neurotoxin into the nasal tissues in need of treatment. In its most general implementation, the invention contemplates the use of carriers that promote the transport of *botulinum* toxin from applied topical compositions. For example, the carrier may be a liquid chemical carrier, such as dimethyl sulfoxide (DMSO). The carrier may also be in the form of a nanoemulsion as described in WO2008/045107. In other embodiments, the carrier may comprise sphingosine and/or cerebroside as described in U.S. Pre-Grant Publication No. 20060182766. The carrier may also comprise a sialoprotein, such as those described, for example in U.S. Pre-Grant Publication No. 20070116724. It is to be understood that the foregoing references, like all references cited herein, are incorporated by reference in their entirety.

Optionally, the topical compositions according to the invention comprise a carrier that includes a positively charged carrier molecule with positively charged efficiency groups attached thereto, as is disclosed, for example, in U.S. Pat. No. 8,398,997, which is hereby incorporated by reference in its entirety. By "positively charged," it is meant that the carrier molecule has a positive charge under at least some solution-phase conditions, more preferably under at least some physiologically compatible conditions. The term "positively charged," as used herein, embraces functionalities that are charged under all pH conditions, for instance, a quaternary amine, as well as functionalities which can acquire positive charge under certain solution-phase conditions, such as pH changes, in the case of primary amines. More preferably, "positively charged" as used herein refers to those groups that have the behavior of associating with anions over physiologically compatible conditions. Polymers with a multiplicity of positively-charged moieties need not be homopolymers, as will be apparent to one skilled in the art. Other examples of positively charged moieties are well known in the prior art and can be employed readily, as will be apparent to those skilled in the art. Without wishing to be limited by theory, it is believed that the positively charged carriers of the invention help to electrostatically anchor the *botulinum* toxin to the treated mucosa, thereby reducing unwanted diffusion, reducing unwanted drainage of the topical formulation into the throat or airway, and increasing efficacy.

In certain embodiments, the positively charged carrier molecule comprises a "positively charged backbone," which is typically a linear chain of atoms, either with groups in the chain carrying a positive charge at physiological pH, or with groups carrying a positive charge attached to side chains extending from the backbone. Preferably, the positively charged backbone itself will not have a defined enzymatic or therapeutic biologic activity. The linear backbone is preferably a hydrocarbon backbone which is, in some embodiments, interrupted by heteroatoms selected from nitrogen, oxygen, sulfur, silicon and phosphorus. The majority of backbone chain atoms are usually carbon. Additionally, the backbone will often be a polymer of repeating units (e.g., amino acids, poly(ethyleneoxy), poly(propyleneamine), polyalkyleneimine, and the like) but can be a heteropolymer. In one group of embodiments, the positively charged backbone is a polypropyleneamine wherein a number of the amine nitrogen atoms are present as ammonium groups (tetra-substituted) carrying a positive charge. Generally, the positively charged backbone will have a molecular weight that ranges from 100-2,500,000, more preferably, 200-2,000,000, even more preferably, 300-500,000, 400-100,000, 500-50,000, 600-20,000 or 700-8,000. Optionally, the positively charged backbone is a nonpeptidyl polymer, which may be a hetero- or homo-polymer such as a polyalkyleneimine, for example a polyethyleneimine or polypropyleneimine, having a molecular weight of from about 500 to about 2,500,000, preferably from about 100,000 to about 1,800,000, and most preferably from about 500,000 to about 1,400,000. Optionally, the nonpeptidyl polymer may have a molecular weight in the range from about 500 to about 5000, about 1000 to about 4000, about 1500 to about 3500, or about 2000 to about 3000. If desired, the backbone may have attached thereto a plurality of side-chain moieties that include positively charged groups (e.g., ammonium groups, pyridinium groups, phosphonium groups, sulfonium groups, guanidinium groups, or amidinium groups). The sidechain moieties in this group of embodiments can be placed at spacings along the backbone that are consistent in separations or variable. Additionally, the length of the sidechains can be similar or dissimilar. For example, in one group of embodiments, the sidechains can be linear or branched hydrocarbon chains having from one to twenty carbon atoms and terminating at the distal end (away from the backbone) in one of the above-noted positively charged groups. In all aspects of the present invention, the association between the carrier and the chemodenervating agent is by non-covalent interaction, non-limiting examples of which include ionic interactions, hydrogen bonding, van der Waals forces, or combinations thereof.

Optionally, the positively charged backbone is a polypeptide having multiple positively charged sidechain groups (e.g., lysine, arginine, ornithine, homoarginine, and the like). For instance, the polypeptide may a molecular weight of from about 500 to about 1,500,000, about 10,000 to about 1,500,000, more preferably from about 25,000 to about 1,200,000, most preferably from about 100,000 to about 1,000,000. If desired, the polypeptide may have a molecular weight in the range from about 500 to about 5,000, about 1,000 to about 4,000, about 1,500 to about 3,500, or about 2,000 to about 3,000. One of skill in the art will appreciate that when amino acids are used in this portion of the invention, the sidechains can have either the D- or L-form (R or S configuration) at the center of attachment. Alternatively, the backbone can be an analog of a polypeptide such as a peptoid. See, for example, Kessler, Angew. Chem. Int. Ed. Engl. 32:543 (1993); Zuckermann et al. Chemtracts-Macromol. Chem. 4:80 (1992); and Simon et al. Proc. Nat'l. Acad. Sci. USA 89:9367 (1992)). Briefly, a peptoid is a polyglycine in which the sidechain is attached to the backbone nitrogen atoms rather than the α-carbon atoms. As above, a portion of the sidechains will typically terminate in a positively charged group to provide a positively charged backbone component. Synthesis of peptoids is described in, for example, U.S. Pat. No. 5,877,278, which is hereby incorporated by reference in its entirety. As the term is used herein, positively charged backbones that have a peptoid backbone construction are considered "non-peptide" as they are not composed of amino acids having naturally occurring sidechains at the α-carbon locations.

A variety of other backbones can be used employing, for example, steric or electronic mimics of polypeptides wherein the amide linkages of the peptide are replaced with surrogates such as ester linkages, thioamides (—CSNH—), reversed thioamide (—NHCS—), aminomethylene (—NHCH$_2$—) or the reversed methyleneamino (—CH$_2$NH—) groups, keto-methylene (—COCH$_2$—) groups, phosphinate (—PO$_2$RCH$_2$—), phosphonamidate and phosphonamidate ester (—PO$_2$RNH—), reverse peptide (—NHCO—), trans-alkene (—CR=CH—), fluoroalkene (—CF=CH—), dimethylene (—CH$_2$CH$_2$—), thioether (—CH$_2$S—), hydroxyethylene (—CH(OH)CH$_2$—), methyleneoxy (—CH$_2$O—), tetrazole (CN$_4$), sulfonamido (—SO$_2$NH—), methylenesulfonamido (—CHRSO$_2$NH—), reversed sulfonamide (—NHSO$_2$—), and backbones with malonate and/or gem-diamino-alkyl subunits, for example, as reviewed by Fletcher et al. ((1998) Chem. Rev. 98:763) and detailed by references cited therein. Many of the foregoing substitutions result in approximately isosteric polymer backbones relative to backbones formed from α-amino acids.

In each of the backbones provided above, sidechain groups can be appended that carry a positively charged group, preferably at physiologic pH. For example, the sulfonamide-linked backbones (—SO$_2$NH— and —NHSO$_2$—) can have sidechain groups attached to the nitrogen atoms. Similarly, the hydroxyethylene (—CH(OH)CH$_2$—) linkage can bear a sidechain group attached to the hydroxy substituent. One of skill in the art can readily adapt the other linkage chemistries to provide positively charged sidechain groups using standard synthetic methods.

Optionally, the positively charged backbone is a polypeptide having efficiency groups. As used herein, an efficiency group is any agent that has the effect of promoting the translocation of the positively charged backbone through a tissue or cell membrane. Non-limiting examples of efficiency groups include -(gly)$_{n1}$-(arg)$_{n2}$ (SEQ ID NO:1), HIV-TAT or fragments thereof, or the protein transduction domain of Antennapedia, or a fragment thereof, in which the subscript n1 is an integer of from 0 to 20, more preferably 0 to 8, still more preferably 2 to 5, and the subscript n2 is independently an odd integer of from about 5 to about 25, more preferably about 7 to about 17, most preferably about 7 to about 13. In a preferred embodiment n1 is 3 and n2 is 7. Still further preferred are those embodiments in which the efficiency group has the formula (gly)$_p$-RGRDDRRQRRR-(gly)$_q$ (SEQ ID NO:2), (gly)$_p$-YGRKKRRQRRR-(gly)$_q$ (SEQ ID NO:3) or (gly)$_p$-RKKRRQRRR-(gly)$_q$ (SEQ ID NO:4) wherein the subscripts p and q are each independently an integer of from 0 to 20 and the fragment is attached to the backbone via either the C-terminus or the N-terminus of the fragment. Preferred efficiency groups are those in which the subscripts p and q are each independently integers of from 0 to 8, more preferably 2 to 5. In some embodiments, the carrier has the amino acid sequence selected from the group consisting of RKKRRQRRR-G-(K)$_{15}$-G-RKKRRQRRR (SEQ ID NO:5), RKKRRQRRR-G-(K)$_{20}$-G-RKKRRQRRR (SEQ ID NO:6), RKKRRQRRR-G-(K)$_{25}$-G-RKKRRQRRR (SEQ ID NO:7), RKKRRQRRR-G-(K)$_{30}$-G-RKKRRQRRR (SEQ ID NO:8), RGRDDRRQRRR-G-(K)$_{15}$-G-RGRDDRRQRRR (SEQ ID NO:9), RGRDDRRQRRR-G-(K)$_{20}$-G-RGRDDRRQRRR (SEQ ID NO:10), RGRDDRRQRRR-G-(K)$_{25}$-G-RGRDDRRQRRR (SEQ ID NO:11), RGRDDRRQRRR-G-(K)$_{30}$-G-RGRDDRRQRRR (SEQ ID NO:12), YGRKKRRQRRR-G-(K)$_{15}$-G-YGRKKRRQRRR (SEQ ID NO:13), YGRKKRRQRRR-G-(K)$_{20}$-G-YGRKKRRQRRR (SEQ ID NO:14), YGRKKRRQRRR-G-(K)$_{25}$-G-YGRKKRRQRRR (SEQ ID NO:15), and YGRKKRRQRRR-G-(K)$_{30}$-G-YGRKKRRQRRR (SEQ ID NO:16). See, e.g., U.S. Pat. No. 8,404,249, and U.S. Pre-Grant Publication No. 20100215591, both of which are incorporated by reference in their entirety.

In another preferred embodiment the positively charged efficiency group is the Antennapedia (Antp) protein transduction domain (PTD), or a fragment thereof that retains activity. (See, e.g., Console et al., J. Biol. Chem. 278:35109 (2003), the contents of which are incorporated by reference in their entirety.) Preferably the positively charged carrier includes side-chain positively charged efficiency groups in an amount of at least about 0.05%, as a percentage of the total carrier weight, preferably from about 0.05 to about 45 weight %, and most preferably from about 0.1 to about 30 weight %. For positively charged efficiency groups having the formula -(gly)$_{n1}$-(arg)$_{n2}$, the most preferred amount is from about 0.1 to about 25%.

In certain embodiments, the backbone portion is a polylysine and positively charged efficiency groups are attached to the lysine sidechain amino groups. In some embodiments, the polylysine may have a molecular weight that ranges from about 10,000 to about 1,500,000, preferably from about 25,000 to about 1,200,000, and most preferably from about 100,000 to about 1,000,000. In certain embodiments, the polylysine may have a molecular weight that ranges from about 500 to about 5000, about 1000 to about 4000, about 1500 to about 3500, or about 2000 to about 3000. The polylysine may be any of the commercially available (Sigma Chemical Company, St. Louis, Mo., USA) polylysines such as, for example, polylysine having MW>70,000, polylysine having MW of 70,000 to 150,000, polylysine having MW 150,000 to 300,000 and polylysine having MW>300,000. The selection of an appropriate polylysine will depend on the remaining components of the composition and will be sufficient to provide an overall net positive charge to the composition and, in some embodiments, provide a length that is preferably from one to four times the combined length of the negatively charged components. Preferred positively charged efficiency groups or efficiency groups include, for example, -gly-gly-gly-arg-arg-arg-arg-arg-arg-arg (-Gly$_3$Arg$_7$) (SEQ ID NO:17) or HIV-TAT fragments, as disclosed herein. In another preferred embodiment the positively charged backbone is a long chain polyalkyleneimine such as a polyethyleneimine or polypropyleneimine. Such polyalkyleneimines, for example, may have a molecular weight of about 1,000,000.

In certain embodiments of this invention, the carrier is a relatively short polylysine or polyethyleneimine (PEI) backbone (which may be linear or branched) and which has positively charged branching groups. Such carriers are useful for minimizing uncontrolled aggregation of the backbones and *botulinum* toxin in a therapeutic composition, which causes the transport efficiency to decrease dramatically. When the carrier is a relatively short linear polylysine or PEI backbone, the backbone will have a molecular weight of less than 75,000, more preferably less than 30,000, and most preferably, less than 25,000. When the carrier is a relatively short branched polylysine or PEI backbone, however, the backbone will have a molecular weight less than 60,000, more preferably less than 55,000, and most preferably less than 50,000. For example, if desired, the backbone may have a molecular weight that ranges from about 500 to about 5000, about 1000 to about 4000, about 1500 to about 3500, or about 2000 to about 3000.

Viscosity Modifiers

The topical *botulinum* toxin compositions for treating rhinitis according to the methods described herein typically also include a viscosity modifier to maintain the location of the applied compositions at the treatment area, to restrict the movement of the compositions from the intended treatment area after application, and/or to minimize or prevent diffusion and inadvertent oral and/or systemic exposure. Generally, the chemical identity of the viscosity modifier is not particularly limited, and may be any pharmaceutically acceptable composition with the appropriate viscosity at the body surface temperature at the area of application, so long as the viscosity modifier is compatible with other components of the topical *botulinum* toxin compositions, as described herein.

The viscosity modifier according to the invention may be chosen such that the viscosity of the topical *botulinum* toxin composition falls within a viscosity range of 10,000-500,000 cps, more preferably, 15,000-250,000 cps, even more preferably 20,000 to 200,000 cps and most preferably 25,000 to 100,000 cps at 25° C. Optionally, the viscosity modifier may be chosen such that the viscosity of the topical *botulinum* toxin composition is ≥1000 cps at 26° C., such as, for example, from 1,000-10,000 cps, 1,500-8,000 cps, 2,000-6,000 cps, or 2,500-5,000 cps. The required amount of viscosity modifying agent can be determined readily by a person of skill in the art, based on the disclosures set forth herein.

The viscosity modifier optionally may be a surfactant. The surfactant may be selected from anionic surfactants, cationic surfactants, zwitterionic surfactants or non-ionic surfactants. In certain embodiments, one or more non-ionic surfactants serve as the viscosity modifier. The non-ionic surfactant can be any commercially available non-ionic surfactant, such as, for example, polyoxyethylene glycol alkyl ethers, polyoxypropylene glycol alkyl ethers, glucoside alkyl ethers, polyoxyethylene glycol octylphenol ethers, polyoxyethylene glycol alkylphenol ethers, glycerol alkyl esters, polyoxyethylene glycol sorbitan alkyl esters, sorbitan alkyl esters, dodecyldimethylamine oxide, block copolymers of polyethylene glycol and polypropylene glycol (polyoxamers) and combinations thereof.

In certain embodiments, the non-ionic surfactant is a polysorbate, non-limiting examples of which include polysorbate 20, polysorbate 40, polysorbate 60, and polysorbate 80. In other embodiments, the non-ionic surfactant is a sorbitan ester, non-limiting examples of which include Span 20, Span 60, Span 65, and Span 80. The invention also contemplates using Triton X-100, trileucine, or NP-40 as the non-ionic surfactants. In addition, the combinations of different non-ionic surfactants are contemplated. In certain preferred embodiments, the non-ionic surfactant is selected from the group consisting of polysorbates, poloxamers, and sorbitans, with polysorbates and sorbitans being particularly preferred.

In a particular embodiment, the viscosity modifier can be a poloxamer. Such poloxamers may be linear or branched, and include tri-blocks or tetra-blocks copolymers. They include poloxamines such as Tetronic and Pluronic. The poloxamer may be chosen from poloxamer 101, poloxamer 105, poloxamer 108, poloxamer 122, poloxamer 123, poloxamer 124, poloxamer 181, poloxamer 182, poloxamer 183, poloxamer 184, poloxamer 185, poloxamer 188, poloxamer 212, poloxamer 215, poloxamer 217, poloxamer 231, poloxamer 234, poloxamer 235, poloxamer 237, poloxamer 238, poloxamer 282, poloxamer 284, poloxamer 288, poloxamer 331, poloxamer 333, poloxamer 334, poloxamer 335, poloxamer 338, poloxamer 401, poloxamer 402, poloxamer 403, poloxamer 407, and combinations thereof. In certain preferred embodiments, the poloxamer that is chosen has a tendency to form a gel with increasing temperature. Non-limiting examples of such poloxamers include poloxamer 188 and poloxamer 407.

As the skilled artisan will appreciate, the amount of viscosity modifying agent that is present in the topical *botulinum* toxin compositions of the invention will depend on the identity of the viscosity modifying agent, as well as the desired viscosity of the topical *botulinum* toxin composition. With this in mind, suitable concentrations for viscosity modifying agent in the topical *botulinum* toxin compositions of the invention may range from about 5% and about 70% (wt/wt), such as, for example, between about 5% and about 60%, between about 10% and about 50%, between about 15% and about 40%. Optionally, the viscosity modifier is present in the compositions in concentration between about 15% and about 20%, such as, for example, about 16%, about 17%, about 18%, about 19% or about 20%. Optionally, the viscosity modifying agent is present in a concentration of 15.0%, 15.5%, 16.0%, 16.5%, 17.0%, 17.5%, 18.0%, 18.5%, 19.0%, 19.5%, or 20% and is selected from the group consisting of poloxamer 212, poloxamer 215, poloxamer 217, poloxamer 231, poloxamer 234, poloxamer 235, poloxamer 237, poloxamer 238, poloxamer 282, poloxamer 284, poloxamer 288, poloxamer 331, poloxamer 333, poloxamer 334, poloxamer 335, poloxamer 338, poloxamer 401, poloxamer 402, poloxamer 403, poloxamer 407, and combinations thereof. For example, in certain preferred embodiments, when the poloxamer is poloxamer 407, the amount of poloxamer present in the formulations of the invention may range from 15-25%, 15.5-24.5%, 16-23%, 16.5-22.5%, 17-22% 17.5%-21.5%, or 18%-21%. Optionally, the amount of poloxamer 407 may be 15.5%, 16.0%, 16.5%, 17.0%, 17.5%, 18.0%, 18.5%, 19.0%, 19.5%, 20%, 20.5%, 21% 21.5% or 22%. Alternatively, the chosen poloxamer may be poloxamer 188, which may be present in the formulations of the invention at a concentration range of 15.5%, 16.0%, 16.5%, 17.0%, or 17.5%. This invention also specifically contemplates adding more than one type of poloxamer to modify the viscosity of the formulation. For instance, if desired, both poloxamer 188 and poloxamer 407 may be added to the formulations of the invention to modify the viscosity.

In addition, the topical formulations according to the present invention may also comprise stabilizing agents. For example, such stabilizing agents may include non-reducing sugars, non-limiting examples of which include trehalose and sucrose. In preferred embodiments, the non-reducing sugar has a glass transition temperature above 55° C., 57° C., or 60° C. Without wishing to be bound by theory, it is believed that such glass transition temperatures are sufficiently high to suppress undesirable molecular motions that cause the *botulinum* toxin to denature. In certain particularly preferred embodiments, the non-reducing sugar is a disaccharide, non-limiting examples of which include trehalose and sucrose. In other embodiments, the non-reducing sugar is a trisaccharide, a non-limiting example of which is raffinose. Generally, the concentration of the non-reducing sugar in the *botulinum* toxin formulations of the invention are in the range of 10% to 40% (w/v), preferably 10% to 25% (w/v), more preferably 15% to 20% (w/v). In some preferred embodiments, the concentration of the non-reducing sugar is 10%, 11%, 12%, 13%, 14%, 15%, 16%, 17%, 18%, 19% or 20% (w/v). When the non-reducing sugar is trehalose, preferably the hydrated form of trehalose (i.e., trehalose-dihydrate) is used to prepare the formulation, although use of the anhydrous form of trehalose is contemplated as well. Since the formulations of the present invention are typically lyophilized, an agent may be added to increase the mechanical strength of amorphous glass solid cake that is formed when the formulation is lyophilized. A non-limiting example of such an agent includes boric acid.

Optionally, the topical *botulinum* toxin formulations of the invention comprise a buffer. Generally, any physiologically compatible buffer capable of maintaining the pH in the range of 4.5 to 6.5, more preferably in the range of 5 to 6, and most preferably about 5.5, is suitable for the *botulinum* toxin formulations of the invention. Non-limiting examples of such buffers include those involving salts of citric acid, acetic acid, succinic acid, tartaric acid, maleic acid, and histidine. Non-limiting examples of suitable buffer concentrations include buffer concentrations in the range of 0.400% to 0.600%; 0.450% to 0.575%, or 0.500% to 0.565%. The invention also contemplates *botulinum* toxin formulations comprising a mixture of buffer salts, non-limiting examples of which include citrate/acetate, citrate/histidine, citrate/tartrate, maleate/histidine, or succinate/histidine. In certain preferred embodiments, the buffer is phosphate buffer.

The topical *botulinum* formulations may also comprise an anti-oxidant that acts as a preservative. Non-limiting examples of such preservatives include butylhydroxytoluene (BHT), methionine, and propyl gallate. One or more of such preservatives may be present in the topical *botulinum* toxin formulations of the invention in a concentration that ranges from 0.3-2.0%, from 0.5%-1.5%, or from 0.75%-1.25%.

Treatment Regimens

The methods described herein can be incorporated into various treatment regimens. For example, the methods for treating rhinitis described herein may be performed on a given patient every one week, two weeks, three weeks, month, two months, three months, four months, five months, six months, seven months, eight months, nine months, ten months, eleven months or twelve months. The length of time between applications will vary depending on many factors, including the specific purified *botulinum* toxin chosen, the dosage (which depends on the concentration of topical composition and the dwell time) and the severity of the rhinitis. As a non-limiting example, purified *botulinum* toxin type A may be administered every three or four months for treating rhinitis, as needed.

Optionally, the topical compositions having a *botulinum* toxin concentration of 1,000-50,000 U/mL may be administered. For example, compositions having a concentration of 2,000 U/mL, 3000, U/mL, 4,000 U/mL, 5,000 U/mL, 6,000 U/mL, 7,000 U/mL, 8,000 U/mL or 9,000 U/mL may be topically applied to the nasal cavity as described herein for a dwell time of 10, 20, 30, 40, or 50 minutes. If desired, topical compositions having a *botulinum* toxin concentration of 5,500 U/mL, 5,750 U/mL, 6,000 U/mL, 6,250 U/mL, 6,500 U/mL, 6,750 U/mL or 7,000 U/mL may be topically applied to the nasal cavity as described herein for a dwell time of 10, 20, 30, 40, or 50 minutes. Alternatively, topical compositions having a *botulinum* toxin concentration of 15,500 U/mL, 15,750 U/mL, 16,000 U/mL, 16,250 U/mL, 16,500 U/mL, 16,750 U/mL or 17,000 U/mL may be topically applied to the nasal cavity as described herein for a dwell time of 10, 20, 30, 40, or 50 minutes. One particularly suitable treatment involves applying 0.2 mL of a topical *botulinum* toxin type A composition containing 6,250 U/mL for a dwell time of 30 minutes. After the dwell time has elapsed, the topical *botulinum* toxin may be flushed out of the patient's nasal cavity by irrigating the nasal cavity with saline solution. As the skilled artisan will appreciate, the resulting effluent contains *botulinum* toxin and is highly toxic. Preferably, the effluent is collected (e.g., absorbed by an absorbent article) and the *botulinum* toxin therein is reacted with an agent to render it no longer toxic. Suitable methods and agents for inactivating *botulinum* toxin include those found, for example, in U.S. patent application Ser. No. 13/334,283, which is hereby incorporated by reference in its entirety.

Formulations

The topical formulations of the invention optionally may be manufactured in a lyophilized form and then reconstituted with a diluent before administration. For example, the lyophilized form may be produced by lyophilizing a liquid composition comprising a *botulinum* toxin, a non-reducing disaccharide or a non-reducing trisaccharide, a non-ionic surfactant, and a physiologically compatible buffer. Typically, in such formulations, the concentration of the non-reducing disaccharide or non-reducing trisaccharide is in the range of 10% to 40% (w/v), the concentration of the non-ionic surfactant is in the range of 0.005% to 0.5% (w/v), and the pH of the liquid composition is in the range of 4.5 to 6.5. See, e.g., U.S. Pre-Grant Publication No. 20100330123, which is hereby incorporated by reference in its entirety. Generally, any pharmaceutically acceptable diluent that does not undergo undesirable reactions with the components of the formulation in question may be used. For example, the formulations may be reconstituted using water, saline, or phosphate buffered saline. Optionally, one or more additives may be included in the diluent to control or improve certain properties of the diluent, non-limiting examples of which include viscosity enhancers (e.g., a poloxamer, such as poloxamer 188 or 407), anti-oxidants (e.g., BHT or methionine), co-solvents (e.g., an alcohol, such as ethanol), and/or tonicity adjusters (e.g., a salt, such as sodium chloride). Exemplary diluents that are suitable for use with the invention include those listed in Tables 3 and 3-1, as set forth herein. For lyophilized formulations that are stored in 2 ml vials, it is often convenient to reconstitute the formulations using 1 ml of diluent, non-limiting examples of which include those shown in Tables 3 and 3-1.

EXAMPLES

Example 1

Topical Formulations

Table 1 shows 35 exemplary lyophilized topical *botulinum* toxin formulations that were prepared in accordance with the present invention. Each formulation was prepared by adding the respective components in the indicated amounts to a standard 2 ml lyophilization vial. The column heading "Toxin (ng/vial)" refers to the amount of *botulinum* toxin type A neurotoxin present (in nanograms per vial), while the column heading "peptide (mg/ml)" refers to the amount of the peptide RKKRRQRRR-Q-(K)$_{15}$-Q-RK-KRRQRRR (SEQ ID NO:18) present (in milligrams per vial). Table 1-1 shows the same 35 exemplary lyophilized topical *botulinum* toxin formulations as in Table 1, except that the numerical entries in Table 1-1 refer to the respective weight percent of the components relative to the total weight of the lyophilized formulation.

TABLE 1

Exemplary topical botulinum toxin formulations

| Formulation | Toxin (ng/vial) | Peptide (mg/vial) | Sodium Citrate dehydrate (mg/vial) | Histidine (mg/vial) | Histidinie Hydrochloride (mg/vial) | Sucrose (mg/vial) | Trehalose (mg/vial) | Methionine (mg/vial) | BHT (mg/vial) | Poloxamer 188 (mg/vial) | Poloxamer 407 (mg/vial) | Trileucine (mg/vial) | Polysorbate 20 (mg/vial) |
|---|---|---|---|---|---|---|---|---|---|---|---|---|---|
| 1 | 11.0 | | 0.45 | 0.10 | | | 20.0 | | | | 10.0 | 0.2 | |
| 2 | 11.0 | 0.030 | 0.45 | 0.10 | | | 20.0 | | | | 10.0 | 0.2 | |
| 3 | 11.0 | 0.030 | 0.45 | 0.10 | | | | 36.0 | | | 0.10 | | |
| 4 | 11.0 | 0.030 | 0.45 | 0.10 | | | 36.0 | | | | 0.10 | | |
| 5 | 11.0 | 0.030 | | | 0.14 | 0.65 | 36.0 | | | | | | |
| 6 | 11.0 | 0.010 | | | 0.14 | 0.65 | 36.0 | | | | | | |
| 7 | 11.0 | 0.003 | | | 0.14 | 0.65 | 36.0 | | | | | | |
| 8 | 11.0 | 0.030 | | | 0.14 | 0.65 | 8.0 | 28.0 | 2.0 | | | | |
| 9 | 11.0 | 0.030 | 0.45 | 0.10 | | | 36.0 | | | | | | |
| 10 | 11.0 | 0.030 | 0.45 | 0.10 | | | | 36.0 | | | | | |
| 11 | 11.0 | 0.030 | 0.45 | 0.10 | | | 8.0 | 28.0 | | | | | |
| 12 | 11.0 | 0.030 | 0.45 | 0.10 | | | 34.0 | | | | | | |
| 13 | 11.0 | 0.030 | 0.45 | 0.10 | | | 36.0 | | | 0.2 | | | |
| 14 | 11.0 | 0.030 | 0.45 | 0.10 | | | 36.0 | | | | | | 0.20 |
| 15 | 1.1 | 0.030 | | | 0.14 | 0.65 | 36.0 | | | | | | |
| 16 | 1.1 | 0.030 | 0.45 | 0.10 | | | 36.0 | | | | | | |
| 17 | 1.1 | 0.030 | | | 0.14 | 0.65 | 8.0 | 28.0 | | | | | |
| 18 | 1.1 | 0.030 | | | 0.14 | 0.65 | 4.0 | 14.0 | | | | | |
| 19 | 1.5 | 0.009 | | 0.45 | 0.10 | | 36.0 | | | | | | 0.10 |
| 20 | 3 | 0.009 | | 0.45 | 0.10 | | 36.0 | | | | | | 0.10 |
| 21 | 6 | 0.009 | | 0.45 | 0.10 | | 36.0 | | | | | | 0.10 |
| 22 | 10 | 0.009 | | 0.45 | 0.10 | | 36.0 | | | | | | 0.10 |
| 23 | 12 | 0.009 | | 0.45 | 0.10 | | 36.0 | | | | | | 0.10 |
| 24 | 25 | 0.009 | | 0.45 | 0.10 | | 36.0 | | | | | | 0.10 |
| 25 | 36 | 0.009 | | 0.45 | 0.10 | | 36.0 | | | | | | 0.10 |
| 26 | 50 | 0.009 | | 0.45 | 0.10 | | 36.0 | | | | | | 0.10 |
| 27 | $5.5 \times 10^3$ | 0.009 | | 0.45 | 0.10 | | 36.0 | | | | | | 0.10 |
| 28 | $1.1 \times 10^4$ | 0.009 | | 0.45 | 0.10 | | 36.0 | | | | | | 0.10 |
| 29 | $2.2 \times 10^4$ | 0.009 | | 0.45 | 0.10 | | 36.0 | | | | | | 0.10 |
| 30 | $1.03 \times 10^4$ | 0.009 | | 0.45 | 0.10 | | 36.0 | | | | | | 0.10 |
| 31 | $2.06 \times 10^4$ | 0.009 | | 0.45 | 0.10 | | 36.0 | | | | | | 0.10 |
| 32 | $4.13 \times 10^4$ | 0.009 | | 0.45 | 0.10 | | 36.0 | | | | | | 0.10 |
| 33 | $5.87 \times 10^4$ | 0.009 | | 0.45 | 0.10 | | 36.0 | | | | | | 0.10 |
| 34 | $8.25 \times 10^4$ | 0.009 | | 0.45 | 0.10 | | 36.0 | | | | | | 0.10 |
| 35 | $1.76 \times 10^5$ | 0.009 | | 0.45 | 0.10 | | 36.0 | | | | | | 0.10 |

TABLE 1-1

Exemplary topical botulinum toxin formulations (amounts expressed in terms of weight percent relative to total weight of the lyophilized formulation)

| Formulation | Toxin ($\times 10^{-5}$) | Peptide | Sodium Citrate dehydrate | Histidine | Histidinie Hydrochloride | Sucrose | Trehalose | Methionine | BHT | Poloxamer 188 | Poloxamer 407 | Trileucine | Polysorbate 20 |
|---|---|---|---|---|---|---|---|---|---|---|---|---|---|
| 1 | 3.6 | | 1.5 | 0.3 | | | 65.0 | | | | 32.5 | 0.7 | 0.0 |
| 2 | 3.6 | 0.1 | 1.5 | 0.3 | | | 65.0 | | | | 32.5 | 0.6 | 0.0 |
| 3 | 4.1 | 0.1 | 1.7 | 0.4 | | | | 97.5 | | | 0.4 | 0.0 | 0.0 |
| 4 | 3.0 | 0.1 | 1.2 | 0.3 | | | 98.1 | | | | 0.3 | 0.0 | 0.0 |
| 5 | 3.0 | 0.1 | | | 0.4 | 1.8 | 97.5 | | | | 0.0 | 0.0 | 0.0 |
| 6 | 3.0 | 0.1 | | | 0.4 | 1.8 | 97.5 | | | | 0.0 | 0.0 | 0.0 |
| 7 | 3.0 | 0.1 | | | 0.4 | 1.8 | 97.5 | | | | 0.0 | 0.0 | 0.0 |
| 8 | 2.8 | 0.1 | | | 0.4 | 1.7 | 20.6 | 71.9 | 5.1 | | 0.0 | 0.0 | 0.0 |
| 9 | 3.0 | 0.1 | 1.2 | 0.3 | | | 98.1 | | | | 0.0 | 0.0 | 0.0 |
| 10 | 4.1 | 0.1 | 1.7 | 0.4 | | | 0.0 | 97.5 | | | 0.0 | 0.0 | 0.0 |
| 11 | 3.0 | 0.1 | 1.2 | 0.3 | | | 21.8 | 76.3 | | | 0.0 | 0.0 | 0.0 |
| 12 | 3.2 | 0.1 | 1.3 | 0.3 | | | 98.0 | | | | | | |
| 13 | 3.0 | 0.1 | 1.2 | 0.3 | | | 97.6 | | | 0.5 | | | |
| 14 | 3.0 | 0.1 | 1.2 | 0.3 | | | 97.9 | | | | | | 0.5 |
| 15 | 3.0 | 0.1 | | | 0.4 | 1.8 | 97.5 | | | | | | |
| 16 | 3.0 | 0.1 | 1.2 | 0.3 | | | 98.1 | | | | | | |
| 17 | 4.8 | 0.1 | | | 0.6 | 2.8 | 34.9 | 61.1 | | | | | |
| 18 | 2.2 | 60.7 | | | | 1.3 | 1.3 | 8.1 | 28.3 | | | | |
| 19 | 0.41 | $2.5 \times 10^{-5}$ | | | 1.2 | 0.3 | 98.2 | | | | | | 0.3 |
| 20 | 0.82 | $2.5 \times 10^{-5}$ | | | 1.2 | 0.3 | 98.2 | | | | | | 0.3 |
| 21 | 1.6 | $2.5 \times 10^{-5}$ | | | 1.2 | 0.3 | 98.2 | | | | | | 0.3 |
| 22 | 2.7 | $2.5 \times 10^{-5}$ | | | 1.2 | 0.3 | 98.2 | | | | | | 0.3 |
| 23 | 3.3 | $2.5 \times 10^{-5}$ | | | 1.2 | 0.3 | 98.2 | | | | | | 0.3 |
| 24 | 6.8 | $2.5 \times 10^{-5}$ | | | 1.2 | 0.3 | 98.2 | | | | | | 0.3 |

TABLE 1-1-continued

Exemplary topical botulinum toxin formulations (amounts expressed in terms of weight percent relative to total weight of the lyophilized formulation)

| Formulation | Toxin ($\times 10^{-5}$) | Peptide | Sodium Citrate dehydrate | Histidine | Histidine Hydrochloride | Sucrose | Trehalose | Methionine | BHT | Poloxamer 188 | Poloxamer 407 | Tri-leucine | Polysorbate 20 |
|---|---|---|---|---|---|---|---|---|---|---|---|---|---|
| 25 | 9.8 | $2.5 \times 10^{-5}$ | | | 1.2 | 0.3 | 98.2 | | | | | | 0.3 |
| 26 | 14 | $2.5 \times 10^{-5}$ | | | 1.2 | 0.3 | 98.2 | | | | | | 0.3 |
| 27 | $1.5 \times 10^3$ | $2.5 \times 10^{-5}$ | | | 1.2 | 0.3 | 98.2 | | | | | | 0.3 |
| 28 | $3.0 \times 10^3$ | $2.5 \times 10^{-5}$ | | | 1.2 | 0.3 | 98.2 | | | | | | 0.3 |
| 29 | $6.0 \times 10^3$ | $2.5 \times 10^{-5}$ | | | 1.2 | 0.3 | 98.2 | | | | | | 0.3 |
| 30 | $2.8 \times 10^3$ | $2.5 \times 10^{-5}$ | | | 1.2 | 0.3 | 98.2 | | | | | | 0.3 |
| 31 | $5.6 \times 10^3$ | $2.5 \times 10^{-5}$ | | | 1.2 | 0.3 | 98.2 | | | | | | 0.3 |
| 32 | $1.1 \times 10^4$ | $2.5 \times 10^{-5}$ | | | 1.2 | 0.3 | 98.1 | | | | | | 0.3 |
| 33 | $1.6 \times 10^4$ | $2.5 \times 10^{-5}$ | | | 1.2 | 0.3 | 98.1 | | | | | | 0.3 |
| 34 | $2.2 \times 10^4$ | $2.5 \times 10^{-5}$ | | | 1.2 | 0.3 | 98.0 | | | | | | 0.3 |
| 35 | $2.2 \times 10^4$ | $2.5 \times 10^{-5}$ | | | 1.2 | 0.3 | 97.8 | | | | | | 0.3 |

Example 2

Topical formulations

Table 2 shows twelve exemplary lyophilized formulations that were prepared according to the invention. Each formulation was prepared by adding the respective components in the indicated amounts to a standard 2 ml lyophilization vial. The column heading "Toxin (ng/vial)" refers to the amount of *botulinum* toxin type A neurotoxin present (in nanograms per vial), while the column heading "peptide (mg/ml)" refers to the amount of the peptide RKKRRQRRR-Q-(K)$_{15}$-Q-RKKRRQRRR (SEQ ID NO:18) present (in milligrams per vial). Table 2-1 shows the same twelve exemplary lyophilized topical *botulinum* toxin formulations as in Table 2, except that the numerical entries in Table 2-1 refer to the respective weight percent of the components relative to the total weight of the lyophilized formulation.

TABLE 2

Exemplary Botulinum Toxin Formulations

| Formulation | Toxin (ng/vial) | Peptide (mg/vial) | Histidine (mg/vial) | Histidine hydrochloride (mg/vial) | Sucrose (mg/vial) | Trehalose (mg/vial) | Sorbitol (mg/vial) | Glycerol (mg/vial) | Boric Acid (mg/vial) | Propyl Gallate (mg/vial) | Polysorbate 20 (mg/vial) |
|---|---|---|---|---|---|---|---|---|---|---|---|
| 36 | 11 | 0.015 | 0.45 | 0.10 | 36.0 | | | | | | 0.10 |
| 37 | 11 | 0.015 | 0.45 | 0.10 | 33.0 | | 3.0 | | | | 0.10 |
| 38 | 11 | 0.015 | 0.45 | 0.10 | 33.0 | | 3.0 | | | 0.10 | 0.10 |
| 39 | 11 | 0.015 | 0.45 | 0.10 | 34.0 | | | | 2.0 | | 0.10 |
| 40 | 11 | 0.015 | 0.45 | 0.10 | | 36.0 | | | | | 0.10 |
| 41 | 11 | 0.015 | 0.45 | 0.10 | | 33.0 | 3.0 | | | | 0.10 |
| 42 | 11 | 0.015 | 0.45 | 0.10 | | 35.0 | | 1.0 | | | 0.10 |
| 43 | 11 | 0.015 | 0.45 | 0.10 | | 34.0 | | 2.0 | | | 0.10 |
| 44 | 11 | 0.015 | 0.45 | 0.10 | | 34.0 | | | 2.0 | 0.10 | 0.10 |
| 45 | 1.1 | 0.015 | 0.45 | 0.10 | 36.0 | | | | | | 0.10 |
| 46 | 1.1 | 0.015 | 0.45 | 0.10 | | 36.0 | | | | | 0.10 |
| 47 | 1.1 | | 0.45 | 0.10 | 36.0 | | | | | | 0.10 |

TABLE 2-1

Exemplary Botulinum Toxin Formulations (amounts expressed in terms of weight percent relative to total weight of the lyophilized formulation)

| Formulation | Toxin ($\times 10^{-5}$) | Peptide | Histidine | Histidine hydrochloride | Sucrose | Trehalose | Sorbitol | Glycerol | Boric Acid | Propyl Gallate | Polysorbate 20 |
|---|---|---|---|---|---|---|---|---|---|---|---|
| 36 | 3.00 | 0.041 | 1.23 | 0.27 | 98.2 | | | | | | 0.27 |
| 37 | 3.00 | 0.041 | 1.23 | 0.27 | 90.0 | | 8.2 | | | | 0.27 |
| 38 | 3.00 | 0.041 | 1.22 | 0.27 | 89.8 | | 8.2 | | | 0.27 | 0.27 |
| 39 | 3.00 | 0.041 | 1.23 | 0.27 | 92.7 | | | | 5.5 | | 0.27 |
| 40 | 3.00 | 0.041 | 1.23 | 0.27 | | 98.2 | | | | | 0.27 |
| 41 | 3.00 | 0.041 | 1.23 | 0.27 | | 90.0 | 8.2 | | | | 0.27 |
| 42 | 3.00 | 0.041 | 1.23 | 0.27 | | 95.5 | | 2.7 | | | 0.27 |
| 43 | 3.00 | 0.041 | 1.23 | 0.27 | | 92.7 | | 5.5 | | | 0.27 |
| 44 | 3.00 | 0.041 | 1.22 | 0.27 | | 92.5 | | | 5.4 | 0.27 | 0.27 |
| 45 | 3.00 | 0.041 | 1.23 | 0.27 | 98.2 | | | | | | 0.27 |
| 46 | 3.00 | 0.041 | 1.23 | 0.27 | | 98.2 | | | | | 0.27 |
| 47 | 3.00 | | 1.23 | 0.27 | 98.2 | | | | | | 0.27 |

Example 3

Reconstitution of Formulations

The lyophilized formulations listed in Tables 1 and 2 generally are used after reconstitution with a diluent. Generally, any pharmaceutically acceptable diluent that does not undergo undesirable reactions with the components contained in the respective formulation may be used. For example, the formulations listed in Tables 1 and 2 may be reconstituted using water, saline, or phosphate buffered saline. Optionally, one or more additives may be included in the diluent to control or improve certain properties of the diluent, non-limiting examples of which include viscosity enhancers (e.g., a poloxamer, such as poloxamer 188 or 407), anti-oxidants (e.g., BHT or methionine), co-solvents (e.g., an alcohol, such as ethanol), and/or tonicity adjusters (e.g., a salt, such as sodium chloride).

For the formulations listed in Tables 1 and 2, it is convenient to reconstitute using 1 ml of diluent, since the formulations are stored in 2 ml vials. Thus, the invention expressly contemplates reconstitution of each formulation listed in Tables 1 and 2 with 1 ml of diluent. Two exemplary diluents that are useful with the formulations of the invention is described below in Tables 3 and 3-1. It is to be understood that the reconstituted formulations of Table 1 recited in Examples 5 and 6 below were reconstituted using the diluent set forth in Table 3, unless otherwise indicated.

TABLE 3

Exemplary Diluent for Reconstituting Formulations

| Component | Function | Amount needed to Reconstitute one 2 ml vial of Drug Product |
|---|---|---|
| Poloxamer 407 | Viscosity Enhancer | 170 mg |
| Butylated hydroxytoluene | Anti-oxidant | 0.1 mg |
| Ethanol | Co-solvent | 0.725 mg |
| Sodium Chloride | Tonicity adjuster | 7.53 mg |
| Water | Solvent | 852.5 mg |

TABLE 3-1

Additional Exemplary Diluent for Reconstituting Formulations

| Component | Function | Amount needed to Reconstitute one 2 ml vial of Drug Product |
|---|---|---|
| Poloxamer 407 | Viscosity Enhancer | 170 mg |
| Sodium Chloride | Tonicity adjuster | 7.53 mg |
| Water | Solvent | 852.5 mg |

Example 4

Topical Formulations

In certain preferred embodiments, the topical formulations of the invention contain botulinum neurotoxin, a carrier peptide, a buffer, a sugar, and a non-ionic surfactant. For instance, certain useful topical formulations may contain $4.1 \times 10^{-6}$-0.22 wt. % botulinum neurotoxin type A, $2.5 \times 10^{-5}$-0.1 wt. % of the peptide RKKRRQRRR-Q-(K)$_{15}$-Q-RKKRRQRRR (SEQ ID NO:18), 1-1.5 wt. % histidine, 0.1-0.5 wt. % histidine hydrochloride, 97-99 wt. % sucrose, and 0.1-0.3 wt. % polysorbate 20. If desired, such formulations may be reconstituted using the diluent set forth in Table 3.

Example 5

Treatment of Allergic Rhinitis

Materials and Methods
Reagents

The following reagents were used: Formulation 22 reported in Table 1 above (reconstituted with the diluent reported in Table 3), a control gel (Revance Therapeutics, Inc., Newark, Calif.), ovalbumin, aluminum hydroxide, gelatin, sodium phosphate, diaminobenzadine (Sigma-Aldrich, St. Louis, Mo.), sheep anti-VIP antibody (Millipore, Billerica, Mass.), biotinylated rabbit anti-sheep antibody and ABC kit (Vector Labs, Burlingame, Calif.), Botulinum toxin type A complex stock solution (Metabiologics Inc., Madison, Wis.).

Animals

Female Sprague-Dawley rats weighing 200-250 g (Charles River Laboratories Inc, Hollister, Calif.) were used in the allergic rhinitis model. Guinea pigs weighing 283-325 g (Charles River, Raleigh, N.C.) were used in the comparative safety study. Animals were housed in a vivarium with a 12 h light/dark cycle and a controlled temperature. Food and water were provided ad libitum. All procedures in this study were performed in accordance with the guidelines detailed in *the Guide for Care and Use of Laboratory Animals* published by the National Academy of Sciences and approved by the Institutional Animal Care and Use Committee.

Ovalbumin-induced Allergic Rhinitis Model

The allergy induction protocol consisted of a series of seven intraperitoneal injections of ovalbumin (0.3 mg) and aluminum hydroxide powder (30 mg) suspension in 0.9% saline (1 mL) administered every other day under anesthesia (~2% isoflurane in $O_2$). Ovalbumin (2 mg) in 0.9% saline (20 μL) was then intranasally instilled daily for a total of seven doses under anesthesia (~2% isoflurane in $O_2$).

Sneezing and nasal itching (indicated by nasal rubbing) are useful indications of allergic rhinitis in rats and represent two of the four traditional clinical symptoms (along with rhinorrhea and congestion) monitored in patients. Consequently, a performance severity assessment (PSA) scale was established to score the extent of these two nasal allergic signs following antigen challenge. Clinical signs were scored prior to induction at baseline, following induction to establish maximal allergic signs on day 0 and on days 3, 5 and 7 following treatment using numerical scores: a) itching (rubbing nose): 0, none; 1, <30 times; 2, 30-50 times; 3, ≥50 times and b) sneezing: 0, none; 1, <3 times; 2, 3-10 times; 3, ≥10 times (30 minute period). The sum of scores for itching and sneezing comprised the composite PSA score.

After completing the induction process, animals which did not respond were excluded from the study. The responding animals were randomly divided into two groups (n=7 per group) and treated with either reconstituted Formulation 22 (0.4 ng dose per rat, equivalent to 100 U of *botulinum* toxin) or control diluent (total volume of 40 μL per rat). Administration of reconstituted Formulation 22 and the control diluent was achieved by inserting a pipette loaded with the appropriate composition into the nasal cavity of the test animals and expelling the composition therein. Administration of intranasal ovalbumin was continued every other day to maintain allergic signs. The animals were evaluated prior to reconstituted Formulation 22 (or control) treatment and post-treatment on days 3, 5 and 7 consistent with the emergence of treatment effect previously reported on day 5 after *Botulinum* neurotoxin type A treatment.

Histological and Immunohistochemical Analysis

Animals were euthanized on day 10 after treatment with reconstituted Formulation 22 or control diluent. The nasal tissues were harvested and fixed in 10% formalin overnight, routinely processed and transversely cut into 5 μm sections at a depth of 1.5 mm from the nostril. Alternating sections were processed for standard hematoxylin and eosin (H&E) staining and vasoactive intestinal peptide (VIP) immunohistochemical staining. The sections for VIP staining were incubated overnight at 4° C. with the sheep anti-VIP antibody (1:1000 dilution). Sections were washed followed by incubation with biotinylated rabbit anti-sheep (1:200 dilution) for 30 minutes at room temperature. VIP immunoreactivity was then visualized using an ABC kit (1:100 dilution) with diaminobenzadine as chromogen.

Safety Testing in Guinea Pigs

Guinea pigs were randomly assigned (three per group) to each dose group with dose levels selected based on previous dose ranging studies. Formulations 27-29 were reconstituted using the diluent described in Example 3 and then administered, one formulation per animal, to each three-animal dose group. Administration was achieved by using a loaded pipette as described above. Following intranasal administration, all animals were observed and weighed daily for the duration of the study. The No Adverse Effect Level (NOAEL) was established as the highest dose causing no adverse clinical observation and no significant difference in mean body weight and overall body weight change compared to controls by t-test. The LD50 was calculated using nominal logistic platform in JMP® 9.0. (SAS Institute Inc.).

Data Analysis

One-way ANOVA was used to assess statistical significance between PSA scores across groups and days of observation. Post-hoc Scheffe tests were performed to assess significance between specific day pairs of observation in the treated animal group. Student's t-test was used for comparison of treatments within treatment day and for comparison of body weights across treatment groups. For statistical significance, a confidence level of $p<0.05$ was used.

Results

Effect of Topical Formulations on Allergic Rhinitis in Rats

Following the initial ovalbumin challenge, both itching and sneezing incidence increased significantly. The PSA score (mean±SEM) increased from 1.0±0.2 to 3.7±0.4 in the treated group ($p<0.01$), and from 1.1±0.1 to 4.3±0.4 in the control group ($p<0.01$). There were no significant differences between the two groups either pre-challenge or post-challenge prior to treatment ($p>0.05$).

Allergic rhinitis severity was assessed on day 3, 5 and 7 after treatment with reconstituted Formulations 22 or the control treatment. The PSA score did not significantly change in the control group, while the PSA score progressively decreased in the reconstituted Formulation 22 group (FIG. 1). One-way ANOVA analysis indicated that the PSA score changes were significantly different between the reconstituted Formulation 22 and control groups ($F=7.277$, $p=0.009$). Subsequent post-hoc Scheffe tests showed that the PSA scores were significantly reduced on days 3, 5 and 7 as compared to pre-treatment in the reconstituted Formulation 22 group ($p<0.05$, $p<0.01$, $p<0.01$, on days 3, 5 and 7, respectively). As compared to the pre-challenge baseline, the PSA score in the reconstituted Formulation 22 group was still significantly elevated on day 3 ($p<0.05$), but the scores on days 5 and 7 did not significantly ($p>0.05$) differ from the normal baseline score indicating that the allergic symptoms were essentially resolved to the normal level by day 5 following reconstituted Formulation 22 treatment. PSA scores for reconstituted Formulation 22 treatment were significantly reduced compared to same day control animals ($p<0.05$). PSA scores for control animals remained significantly elevated ($p<0.01$) from normal baseline throughout the experiment indicating the sustained induction of allergic rhinitis clinical signs in the model throughout the course of the experiment.

Figure 2:
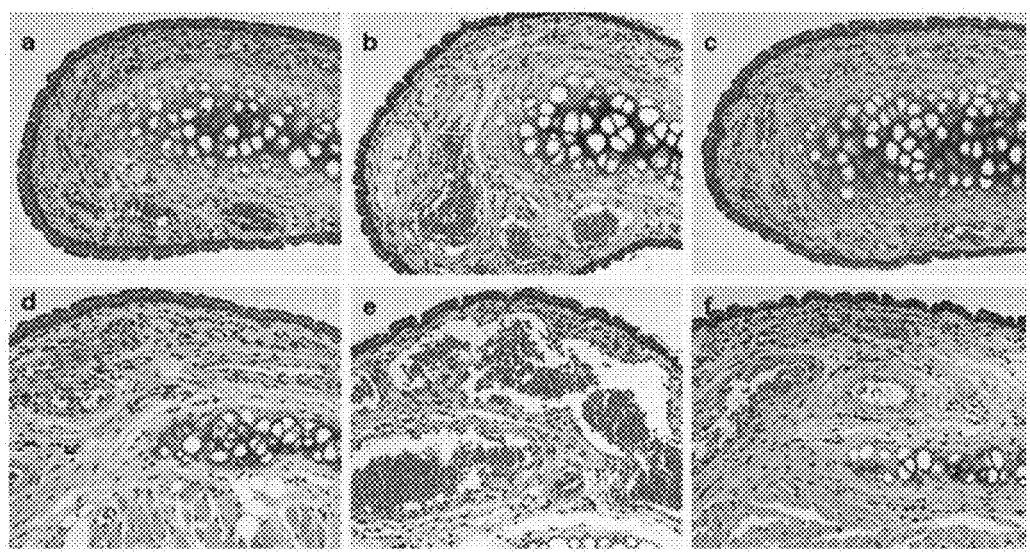
FIG. 2. Effect of reconstituted Formulation 22 on inflammatory pathology associated with allergic rhinitis in nasal tissue. Histological staining of corresponding region of (a-c) left turbinate and (d-f) lateral nasal wall from three animals, (a,d) normal animal, (b, e) allergic control, and (c, f) allergic reconstituted Formulation 22 treated, respectively. The thickness of nasal mucosa was greater in (b, e) control animals than in (a, d) normal and (c, f) reconstituted Formulation 22-treated allergic animals. Remarkable mucosal edema, congestion and vascular dilatation were noted in (b, e) control animals when compared with (a, d) normal animals and (c, f) reconstituted Formulation 22-treated animals. (c, f) The reconstituted Formulation 22-treated animals showed essentially normal nasal mucosal tissue with only mild congestion (hematoxylin and eosin [H&E] stain; original magnification, ×20).

Histological and Immunohistochemical Evaluation of Topical Formulation Treatment Effects The H&E stained sections of control animals revealed typical signs of inflammatory pathology including edema, congestion and vascular dilatation in nasal mucosa across the cavity, particularly in turbinate (FIG. 2b) and lateral nasal wall (FIG. 2e), as compared to normal control animals (FIGS. 2a and d). Reconstituted Formulation 22 treatment resulted in essentially complete resolution of inflammatory findings (FIG. 2). Additionally, hyperplasia of serous glands also was found in some control animals (FIG. 2b). The nasal mucosa of reconstituted-Formulation 22-treated animals (FIGS. 2c and f) appeared essentially normal with only mild congestion (i.e. on lateral nasal wall of this animal specimen shown in FIG. 2e) on day 10 after treatment. No signs of atrophy or degeneration of serous glands were found after the reconstituted Formulation 22 treatment.

Figure 3:
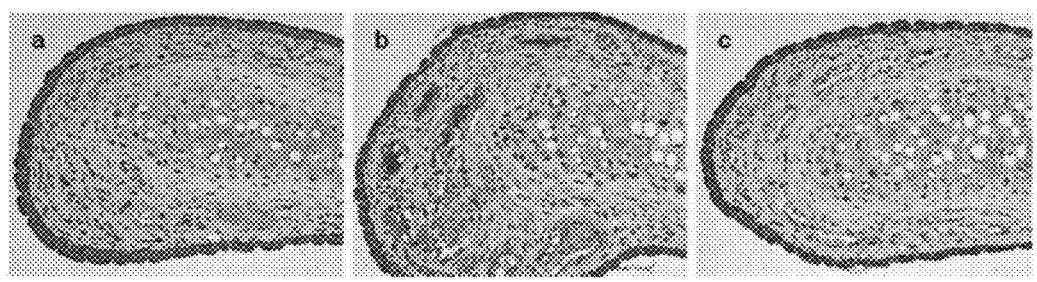
FIG. 3: Immunohistochemical localization of vasoactive intestinal peptide in nasal turbinate. Serial sections from tissues shown in FIG. 2, a-c, were prepared and stained for vasoactive intestinal peptide (VIP) expression (indicated by dark staining). Strong VIP expression was noted in (b) control animals when compared with (a) normal animals. (c) After reconstituted Formulation 22 treatment, VIP expression was down-regulated essentially to normal levels (original magnification, ×20).

VIP expression was dramatically increased following ovalbumin challenge and observed in the control animals (FIG. 3b) in contrast to the normal animals (FIG. 3a), especially around blood vessels and serous glands. Following reconstituted Formulation 22 treatment, VIP expression in the nasal mucosa decreased markedly (FIG. 3c) and appeared comparable to normal animal tissue samples (FIG. 3a).

Figure 4:
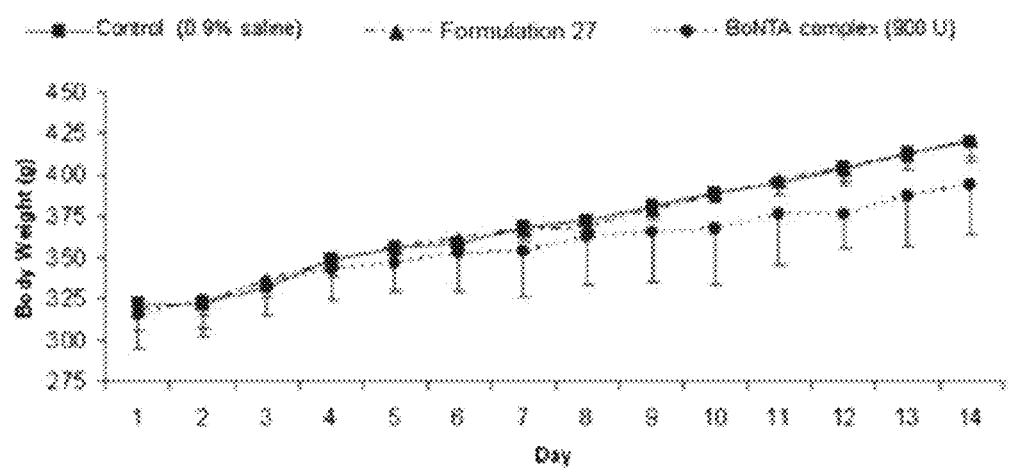
FIG. 4: Graph indicating effects of *botulinum* neurotoxin type A (BoNTA) complex (900 U, ●), reconstituted Formulation 27 (27,500 U, ▲) and saline control (■) on mean daily weight of guinea pigs. Animals received a single intranasal dose of reconstituted Formulation 27, 27,500 U (OE); BoNTA complex, 900 U (F); or saline control (f). Each symbol represents the average of three animals with SD shown by error bars. Asterisks denote values for reconstituted Formulation 27 that were significantly reduced compared with same day values for control (p<0.05).

Safety Evaluation of Reconstituted Formulations Compared to *Botulinum* Neurotoxin Type Complex in Guinea Pigs The safety profile of reconstituted Formulations 27-29 following intranasal dosing was compared to *botulinum* type A complex in guinea pigs which are highly sensitive to the toxic effects of *botulinum* type A complex, thus providing a conservative estimate of safety for reconstituted Formulation 27-29 (FIG. 4). Death was observed in groups of animals treated with 110000 U of reconstituted Formulation 29, and 1800 U and 3600 U of *botulinum* type A complex. The LD50 for reconstituted Formulations 27-29 and *botulinum* type A complex via intranasal route of administration was determined as 108350 U and 1836 U, respectively. Dose levels of reconstituted Formulation 28 up to 55000 U/animal were well tolerated with no abnormal clinical observations and no significant difference in mean daily body weight or overall body weight gain as compared to control ($p=0.2278$ body weight gain). There was no significant difference in mean daily body weight or overall body weight gain of animals treated with *botulinum* type A complex at 900 U ($p=0.1963$ for body weight gain) compared to control. The No Adverse Effect Level (NOAEL) observed for intranasal dosing of guinea pigs was 27500 U/animal for reconstituted Formulation 27 and 900 U/animal for *botulinum* type A complex, indicating reconstituted Formulations 27-29 are approximately 31-fold safer compared to *botulinum* type A complex via the intranasal route of administration. Further, this NOAEL dose in guinea pigs is approximately 250-fold higher than the dose shown to be effective in treating allergic rhinitis in the rat model.

Discussion

The PSA scale was shown to be sensitive and specific in tracking the onset of clinical signs of rhinitis. The typical total nasal symptom score used in clinical studies of rhinitis treatments tracks sneezing, itching, rhinorrhea and congestion. For this study clinical observation of animals permitted quantitation of sneezing and itching (nasal rubbing) whereas congestion was addressed qualitatively as part of the histopathology assessment. Rhinorrhea was difficult to quantitate in rats and thus not included, however, it generally tracks with the other symptoms when evaluated in clinical treatment of rhinitis. Treatment with reconstituted Formulation 22 but not control resulted in significant reduction in PSA score by day 3 following treatment as compared to control and with essentially full resolution to normal baseline levels by day 5. In accordance with previous studies that treated rhinitis by injecting *botulinum* type A complexes in animals and in humans, these results indicate that the topical intranasal application of reconstituted Formulation 22 also can relieve clinical signs in a rat model of allergic rhinitis.

Histological staining of nasal tissues of allergic animals revealed significant degrees of mucosal edema, congestion and vascular dilatation along with hyperplasia of serous glands which were resolved to essentially normal baseline levels following reconstituted Formulation 22 treatment. This effect of reconstituted Formulation 22 treatment on the inflammatory response associated with allergic rhinitis was further characterized by showing that the tissue level of VIP, a known mediator of nasal glandular secretions and the inflammatory process, was reduced essentially to normal levels following reconstituted Formulation 22 treatment.

Allergic rhinitis is caused by the interaction of allergens with inflammatory cells, resulting in release of vasoactive and proinflammatory mediators within the nasal mucosa. Regulatory peptides, such as VIP, may play an important role in the hypersecretion of allergic rhinitis where a high density of VIP expression has been shown in nasal mucosa in allergic rhinitis patients and rats. It is therefore noteworthy that reconstituted Formulation 22 treatment reduced VIP expression to baseline levels and the suppression of VIP activity is associated with the reduction of congestion, vascular dilatation and edema.

The current study shows that Formulation 22, reconstituted as described above, provides efficient transmucosal penetration in this rat model, eliminating the need for treatment by injection or nasal sponge packing, as reported in previous studies. Transmucosal flux of *botulinum* neurotoxin type A and the gel nature of reconstituted Formulation 22 helps to localize the applied dose to the intended treatment site, thereby limiting spread of liquid *botulinum* type A to the gut via nasopharyngeal drainage and potential systemic toxicity. This safety profile of reconstituted Formulations 27-29 were confirmed in the comparative safety study with *botulinum* type A complex in guinea pigs showing reconstituted Formulations 27-29 to be approximately 31-fold safer compared to *botulinum* type A complex. The No Adverse Effect Level (NOAEL) dose in guinea pigs is approximately 250-fold higher than the dose shown to be effective in treating allergic rhinitis in the rat model thus providing a large therapeutic window in preclinical models.

Example 6

Safety Profile of Purified *Botulinum* Neurotoxin Type A

Materials and Methods
Reagents

Reconstituted Formulation 25 as described above was manufactured at Revance Therapeutics, Inc. (Newark, Calif.), and *botulinum* type A complex was purchased from Metabiologics (Madison, Wis.) as a 1 mg/mL solution. Simulated gastric fluid (SGF) and simulated intestinal fluid (SIF) were prepared per United States Pharmacopeia. In some cases, the SGF was used without addition of pepsin to study the contribution of the enzyme.

Animals

Male rats, weighing 200-250 g, were purchased from Charles River Laboratories (Hollister, Calif.). The use of animals in this study was approved by the local Institutional Animal Care and Use Committee (IACUC). Rats were housed in a vivarium with a 12 h light/dark cycle and controlled temperature. Food and water were provided ad libitum.

Oral Toxicity

A single dose 14-day oral toxicity study in rats was conducted comparing oral toxicity of reconstituted Formulations 30-35 and *botulinum* type A complex. Animals (fed state) were dosed via oral gavage at 4 mL/kg. For reconstituted Formulations 30-35, rats were dosed with $1.03 \times 10^7$ up to $1.76 \times 10^8$ U/kg of toxin using a pipette as described in Example 1. For *botulinum* type A complex dose group, rats were dosed with $1.31 \times 10^5$ up to $4.20 \times 10^6$ U/kg. These dose ranges were based on preliminary dose ranging studies (data not shown). All animals were observed and weighed daily throughout the course of the study. The NOAEL was established as the highest dose causing no adverse clinical observation and no significant difference in mean body weight and overall body weight change compared to controls by t-test (Excel 2003, Microsoft, Washington, USA). The $LD_{50}$ was calculated using the nominal logistic platform in JMP® 9.0. (SAS Institute Inc., NC, USA).

In Vitro Assays in Gastrointestinal Model

In order to study the gastric effect on toxin stability, reconstituted Formulation 25 and *botulinum* type A complex were incubated in SGF at 9000 U/mL at 37° C. The potency of reconstituted Formulation 25 and *botulinum* type A complex were measured at T=0 and at each subsequent time point. Due to the differences in stability profile of reconstituted Formulation 25 and *botulinum* type A complex, reconstituted Formulation 25 and *botulinum* type A complex were incubated in SGF using adjusted time courses. In the case of reconstituted Formulation 25, the toxin was exposed to SGF for less than one minute before diluted for potency testing due to rapid inactivation. In the case of *botulinum* type A complex, potencies were tested on samples taken at 5 minute, 15 minutes, 30 minutes, and 60 minutes.

Proteolysis Effects

In order to study the enzymes effects on toxin stability, reconstituted Formulation 25 and *botulinum* type A complex were incubated in SGF at 9000 U/mL at 37° C. with pepsin. Again, the potency of reconstituted Formulation 25 and *botulinum* type A complex were measured at T=0 and at each subsequent time point; in the case of reconstituted Formulation 25, the toxin was exposed to SGF for less than one minute before dilution for its potency test. In the case of botulinum type A complex, samples were taken at 5° minute, 15° minutes, 30° minutes, 1° hour, and 2° hours for its potency test.

In order to study the enzymes effect on toxin stability in SIF, reconstituted Formulation 25 and botulinum type A complex were incubated in SIF for up to 2 hours. Samples taken at 0, 30 minutes, and 2 hours were tested for potency.

In order to mimic the normal physiological pattern where the toxin is first exposed to gastric fluid and then exposed to intestinal fluid, a separate experiment was conducted wherein reconstituted Formulation 25 and botulinum type A complex were first incubated in SGF for 30 minutes, then transferred to SIF and further incubated for up to 2 hours. Samples taken at 0, 30 minutes, and 2 hours were tested for their potency. Samples from each test condition were tested in mouse potency assay via intraperitoneal (IP) injection for lethality at 72 hr. Dose response data were analyzed using the nominal logistic platform in JMP® 9.0. (SAS Institute Inc.) to derive an LD50 value and to calculate relative potency compared to a reference standard material.

Data analysis. For each time course study, the potency at T=0 was measured. The potency at each subsequent time point was expressed as the percentage of T=0, % Potency=$T_{x\ minutes}/T_0 \times 100\%$ In botulinum type A complex stability study in SGF, the logarithmic curve fits were formatted using Microsoft Office Excel 2003 (Microsoft, Redmond, Wash., USA) to compute the half-life of BoNTA complex stability. The half-life was then calculated.

Results

Oral Toxicity

To further characterize the safety profile of reconstituted Formulations 30-35 following oral dosing and to compare reconstituted Formulations 30-35 with conventional botulinum type A complex, rats were dosed orally via gavage with escalating doses to determine oral LD50 and NOAEL for the two toxin formulations. Death was observed in groups of animals treated with higher than $2.06 \times 10^7$ U/kg of reconstituted Formulation 31, and $2.63 \times 10^5$ U/kg of botulinum type A complex (Table 4). The oral LD50 for reconstituted Formulations 30-35 and botulinum type A complex was determined to be $1.19 \times 10^8$ U/kg and $5.03 \times 10^6$ U/kg, respectively.

TABLE 4

| Test article | Dose in LD50 U (U/kg) | Formulation | Dose response (#death/total # tested) |
|---|---|---|---|
| Topical Formulation | 1.76E+08 | 35 | 1/3 |
| | 8.25E+07 | 34 | 3/6 |
| | 5.87E+07 | 33 | 0/3 |
| | 4.13E+07 | 32 | 1/6 |
| | 2.06E+07 | 31 | 2/6 |
| | 1.03E+07 | 30 | 0/6 |
| botulinum type A complex | 4.20E+06 | | 1/3 |
| | 1.40E+06 | | 1/3 |
| | 5.25E+05 | | 1/6 |
| | 4.66E+05 | | 0/3 |
| | 2.63E+05 | | 1/12 |
| | 1.31E+05 | | 0/6 |

Animals dosed with toxin concentrations of $1.03 \times 10^7$ U/kg of reconstituted Formulation 30 or $1.31 \times 10^5$ U/kg of botulinum type A complex showed no abnormal clinical observations and no significant difference in mean daily body weight or overall body weight gain as compared to control (p=0.4952 and 0.4163 for body weight gain reconstituted Formulation 30 and botulinum type A complex, respectively), indicating reconstituted Formulation 30 is approximately 80-fold less toxic compared to botulinum type A complex via the oral route of administration on a unit-for-unit basis.

In Vitro Assays

To further characterize the distinct oral safety profiles of botulinum type A complex and reconstituted Formulation 25 observed in vivo, comparison was made using SGF and SIF model systems. Incubation of reconstituted Formulation 25 in SGF resulted in complete loss of detectable activity within one minute of incubation consistent with a half-life of less than 6 seconds (lower limit of detection for the potency assay is 0.1% of starting activity, i.e., ten half-lives of decay). In contrast, botulinum type A complex slowly lost its activity with a half-life of 9 minutes.

Besides pH extremes, the other stresses that the botulinum neurotoxin type A must endure come from proteases, such as pepsin in the gastric fluid. There was no detectable difference in reconstituted Formulation 25 stability in SGF in the presence of pepsin; interestingly, the stability of botulinum type A complex in SGF is enhanced in the presence of pepsin with a half-life of nearly 17 minutes, almost double the half-life in the absence of pepsin and at least 170-fold greater than reconstituted Formulation 25.

When incubated in SIF, both botulinum type A formulations were susceptible to protease digestion where reconstituted Formulation 25 was degraded faster than botulinum type A complex, indicating the non-toxin accessory proteins protect the toxin from enzyme digestion (Table 5). However, incubation of the botulinum type A complex in SGF (pepsin at pH 1.2) prior to exposure of the complex to SIF actually enhanced the stability of botulinum type A complex in SIF (Table 6) exhibiting a half-life approximately 30 minutes. Thus, under conditions that simulate the path of the botulinum type A complex through the gastrointestinal tract (i.e., gastric exposure followed by intestinal exposure), the non-toxic components of the complex protected botulinum neurotoxin from proteolysis and actually enhanced subsequent stability in SIF whereas reconstituted Formulation 25 was very rapidly inactivated in SGF and did not exhibit any detectable activity in the intestinal environment. When reconstituted Formulation 25 was first incubated in SGF and then in SIF, no toxin activity was observed, indicating the SGF caused changes in the toxin protein which were not recovered in SIF.

TABLE 5

| | Time (minutes) | | |
|---|---|---|---|
| | 0 | 30 | 120 |
| reconstituted Formulation 25 | 100.0% | 0% | 0% |
| botulinum type A complex | 100.0% | 4.1% | 0.7% |
| botulinum type A complex (pre-incubation in SGF) | 100% | 46.5% | 3.6% |

TABLE 6

| | Half-life (min) | |
|---|---|---|
| Condition | botulinum type A complex | reconstituted Formulation 25 |
| SIF | <2 | <0.1 |
| Pre-incubation in SGF | 26 | <0.1 |

Discussion

The differences in reported safety margin of 150 kDa to *botulinum* type A complex may due to the differences in toxin preparations/formulation and the methods used to detect toxin biological activity. In this study, the oral toxicity of *botulinum* type A complex was significantly greater than that observed for purified 150 kDa neurotoxin. The oral $LD_{50}$ values for reconstituted Formulations 30-35 and *botulinum* type A complex were determined to be $1.19 \times 10^8$ U/kg and $5.03 \times 10^6$ U/kg, respectively; the NOAEL for reconstituted Formulation 30 and *botulinum* type A complex were $1.03 \times 10^7$ U/kg and $1.31 \times 10^5$ U/kg, respectively, indicating reconstituted Formulation 30 was approximately 80-fold less toxic compared to *botulinum* type A complex via the oral route of administration. Reconstituted Formulation 25 bioactivity was undetectable within one minute in SGF with a half-life of less than 6 seconds whereas the half-life of the BoNTA complex was approximately 17 minutes in SGF. The intestinal stability of *botulinum* type A complex SIF was enhanced by >10 fold if the toxin was pre-incubated in SGF, whereas when reconstituted Formulation 25 was first incubated in SGF and then in SIF, no toxin activity was observed, indicating the gastric fluid caused irreversible loss of activity. These findings in vitro may underlie the mechanism by which reconstituted Formulation 30, when dosed orally in rats, is approximately 80 times less toxic than *botulinum* type A complex due to its instability in the gastric and intestinal fluids, the natural path of neurotoxin through gastrointestinal tract when ingested.

Example 7

Phase 2 Clinical Trial to Evaluate Safety and Efficacy of *Botulinum* Toxin Type A Topical Gel in Treating Allergic Rhinitis Design and Methodology A double-blind, randomized, placebo controlled study was conducted with 51 subjects enrolled. Subjects were enrolled in one of two (2) parallel treatment groups with 26 subjects in the test article group and 25 subjects in the control group, following satisfaction of entry criteria and screening procedures. Each subject received either a test article or placebo.

Subjects

Subjects participating in the study met the following eligibility criteria:
- predominately seasonal allergic rhinitis with a history of seasonal allergic rhinitis, for at least 12 months, having required intervention/medication and confirmed by documented medical history;
- confirmed as reactive to rye grass seasonal allergen on skin prick testing (greater than 3 mm) or positive blood specific IgE testing rye grass allergen, within the prior 12 months;
- total nasal symptom score of at least 7 (using a composite scale of 0-12 based on 0-3 scales for each of four symptoms) averaged from screening to treatment (day 0);
- outpatient, male or non-pregnant, non-nursing females, 18-65 years of age, in good general health;
- female subjects of childbearing potential having a negative urine pregnancy test result at baseline and practicing a reliable method of contraception throughout the study; and
- willing to refrain from use of medications for rhinitis symptoms (such as decongestants, corticosteroids—oral, inhaled and nasal sprays) for 1 week prior and 2 weeks post treatment.

Test Article/Placebo, Dose, and Mode of Administration

The test article in this Example was a topical gel containing "Formulation 24", as listed above in Table 1. Formulation 24 was used to prepare the topical gel formulation, which was composed of 25 ng/vial purified and lyophilized 150 kDa *botulinum* toxin type A and approximately 9 mcg/mL of the absorption enhancing peptide excipient, reconstituted with 1.0 mL of a poloxamer diluent, along with inactive ingredients, giving a concentration of 25 ng/mL or 5 ng/0.2 mL. The peptide excipient used was the antimicrobial peptide having amino acid sequence, Arg-Lys-Lys-Arg-Arg-Gln-Arg-Arg-Arg-Gly-(Lys)$_{15}$-Gly-Arg-Lys-Lys-Arg-Arg-Gln-Arg-Arg-Arg (SEQ ID NO:5). The poloxamer diluent used was 16.5% poloxamer 407 and 0.9% sodium chloride in water, with BHT and ethanol (see Table 3). Other inactive ingredients included histidine, histidine hydrochloride, sucrose, and polysorbate 20, in the amounts provided above in Table 1.

Approximately 0.2 mL total volume (5 ng) of the test article was used as the applied test dose, using topical administration. (The peptide enables the delivery of *botulinum* toxin to the underlying tissue.) The placebo comprised a topical gel formulation of only the inactive ingredients of Formulation 24 (histidine, histidine hydrochloride, sucrose, and polysorbate 20, in the amounts provided above in Table 1), reconstituted with the poloxamer diluent. Again approximately 0.2 mL total volume was used as the applied placebo dose, using topical administration. Accordingly, a dose of 5 ng of the test article was compared to placebo.

The topical gels were prepared by an unblinded, trained study staff member. Formulation 24 and control were supplied in a professional, single-use reconstitution/administration apparatus, containing a vial of lyophilized *botulinum* toxin Type A, as the active pharmaceutical ingredient (25 ng/mL or placebo), formulated with peptide excipient (9 mcg/mL), and other inactive ingredients. The apparatus also contained a cartridge of poloxamer diluent for reconstitution. The placebo control was a lyophilized vial of inactive ingredients. The reconstituted formulations provided the gels for topical application.

For each subject, 0.5 mL of gel containing either Formulation 24 or placebo was divided between four swabs, with two swabs for each of the two nostrils, for application to the inferior turbinates and adjoining intranasal mucosal surfaces using a nasal speculum. Some of the product was absorbed by the swab, and left on the swab. Thus, while 0.5 mL of gel was used to wet swabs, this lead to a transfer of approximately 0.2 mL to the target dose site. Specifically, swab recovery studies based on mass transfer showed that when one loads gel (containing Formulation 24 or placebo) onto a swab, where approximately 0.117 g of gel was loaded on a swab, approximately 0.083 g of gel was recovered on the swab after application in accordance with study protocol, indicating that approximately 0.034 g of gel was applied intranasally. It follows then that using a total of four swabs (two per nostril), the total amount of gel transferred was approximately 0.034 g×4, which equals approximately 0.136 g of gel. As the density of the gel was 1.027 g/mL, approximately 0.132 mL of gel was calculated to have been applied intranasally to each subject. This value was rounded up to 0.2 mL, as a conservative estimate for safety in the clinical trial.

Subjects received a single intranasal application of either the test article (containing Formulation 24) or a matched placebo gel on day 0. The gel was allowed to remain on for 30 minutes and then removed by saline flush. Subjects were monitored for safety throughout the study, at day 2 and weeks 2, 4, and 8, and for local irritation of treatment areas at baseline and post-treatment day 0 and day 2.

Efficacy Assessments

Efficacy was assessed by total nasal symptom (TNS) score, Rhinoconjunctivitis Quality of Life Questionnaire (RQLQ), peak nasal inspiratory flow (PNIF), and peak expiratory flow (PEF) with forced expiratory volume (FEV1), all recorded by the subject and reported at baseline and weeks 2, 4, and 8.

TNS-4 score is the sum of individual scores for rhinorrhea, nasal congestion, nasal itching, and sneezing, each measured on an ordinal scale of 0, 1, 2 or 3, representing no symptoms, mild, moderate, or severe symptoms, respectively. The individual components of the TNS score are recorded by the subject daily and reported at follow-up visits (pre- and post-allergen challenge where applicable).

RQLQ is a questionnaire measuring the functional problems (physical, emotional, social, and occupational) most troublesome to adults with either seasonal or perennial or allergic or non-allergic rhinoconjunctivitis (see, Juniper E F, et al. Development and testing of a new measure of health status for clinical trials in rhinoconjunctivitis. *Clin Exper Allergy* 1991; 21: 77-83., 1991, which is hereby incorporated by reference in its entirety). The RQLQ includes 28 questions in 7 domains (activity limitation, sleep problems, nose symptoms, eye symptoms, non-nose/eye symptoms, practical problems, and emotional function) of which 3 are 'patient-specific' questions in the activity domain, allowing patients to select 3 activities where there are most limited by their rhinoconjunctivitis. Patients recall how bothered they were by their rhinoconjunctivitis during the previous week and respond to each question on a 7-point scale (0=not affected-6=extremely affected). The overall RQLQ score is the mean of all 28 responses and the individual domain scores are the means of the items in those domains. The RQLQ has been validated and used extensively throughout the world in clinical practice and clinical trials (see Juniper E F, et al. Validation of a standardised version of the Rhinoconjunctivitis Quality of Life Questionnaire. *J Allergy Clin Immunol* 1999; 104: 364-9).

As an additional efficacy assessment, allergen challenge was performed at baseline and week 4, wherein the subject was exposed to cognate allergen (subject confirmed as reactive by prior skin test; allergen extract applied to nasal septum on paper filter disk), and nasal symptoms and PNIF were recorded post-challenge.

A quantitative airflow measure also was employed. Specifically, due to the high comorbidity of bronchial reactivity (which would change both mouth and nasal airflow), the measure of nasal resistance to flow was measured as a pure rhinitis quantitative measure. This represents the difference between nasal and mouth air flow. The smaller the gap, the less nasal resistance was present.

Efficacy Evaluations

Efficacy assessments were performed at baseline and weeks 2, 4, and 8 by:

total nasal symptom score: combination of rhinorrhea, nasal congestion, nasal itching, and sneezing, recorded daily by each subject and reported at visits (pre- and post-allergen challenge where applicable);

individual nasal symptom scores for rhinorrhea, nasal congestion, nasal itching and sneezing, recorded daily by subject and reported at visits and scored at office visit (pre- and post-allergen challenge where applicable);

rhinoconjunctivitis quality of life questionnaire (RQLQ) completed weekly by subjects; and peak nasal inspiratory flow (PNIF) with peak expiratory flow (PEF) by the subject daily and at visits (pre- and post-allergen challenge where applicable).

Safety Assessments

Clinical Laboratory Data: As outlined in Table 7, non-fasting samples for chemistry were collected at screening and week 8 (or early discontinuation).

TABLE 7

| Clinical Laboratory Tests | | | |
|---|---|---|---|
| Serum Chemistry | Hematology | Urinalysis | Additional Tests |
| Glucose | Hemoglobin | Specific gravity | Urine Pregnancy (WOCBP only) |
| Total bilirubin | Hematocrit | pH | |
| Alanine aminotransferase | Total and differential leukocyte count | Glucose | Serum pregnancy test at week 8 (or early discontinuation) if UPT is positive |
| Aspartate aminotransferase | | Protein | |
| Alkaline phosphatase | Red blood cell count | Blood | |
| Blood Urea Nitrogen | Platelet count | Bilirubin | |
| | | Ketones | |

Pregnancy Testing: All women of childbearing potential had a urine pregnancy test at screening and treatment (day 0) and if either result was positive, the subject was not allowed to participate in the study. Women of childbearing potential also had a urine pregnancy test at their final study visit (week 8 or early discontinuation). If the test was positive, the pregnancy was confirmed by a serum pregnancy test.

Local Irritation Assessment: All application sites were evaluated for any irritation, pre-treatment and post-treatment, using the Erythema Assessment (Table 8) and the Clinical Signs/Symptoms Descriptors (Table 9).

TABLE 8

| Erythema Assessment | |
|---|---|
| Rating | Description |
| 0 | No reaction/No erythema |
| 1 | Minimal erythema (barely perceptible) |
| 2 | Strong erythema (easily visible) |
| 3 | Strong erythema, spreading outside of treated site |
| 4 | Strong erythema, spreading outside of treated site with either edema (swelling) or vesicles (elevated, circumscribed lesions up to 1 cm in size that are filled with serous fluid) |
| 5 | Severe reaction with ulceration (irregularly sized and shaped erosions) |

TABLE 9

Clinical Signs/Symptom Descriptors

| Descriptor | Description |
|---|---|
| O | No Clinical Signs/Symptoms |
| E | Edema (swelling) |
| S | Scaling (shedding of dead cells) |
| F | Fissures (linear breaks in the mucosa) |
| C | Crusts (colored masses of exudates) |
| V | Vesicles (blistering) |
| BS | Burning or stinging (sensation as described by the subject) |
| I | Itching (sensation as described by the subject) |

The overall scoring system involved an erythema rating scale plus the addition of clinical descriptors adapted from Dykes P J, et al. An evaluation of the irritancy potential of povidine iodine solutions: comparison of subjective and objective assessment techniques. *Clin Exp Dermatol* 1992; 17(4):246-9, which is hereby incorporated by reference in its entirety. The severity of erythema was rated on a scale of 0-5, along with the presence of other clinical signs or symptoms. These descriptors were noted by letters are then added to the numerical score (e.g., strong erythema spreading outside the treatment site with subject reporting scaling =3 S).

Cranial Nerves I-VII: Evaluation of cranial nerves I-VII was performed at treatment (pre-application), day 2, and weeks 2, 4, and 8 (or early discontinuation). Scores for each cranial nerve was captured as outlined in Table 10 (for examination procedures and criteria, see Bates B. A guide to physical examination and history taking. J. B. Lippincott & Co. 6th edition (1995) Chapter 7:168-169, 172-175; Chapter 18:505-8, which is hereby incorporated by reference in its entirety).

TABLE 10

Cranial Nerve Assessment

| Rating | Description |
|---|---|
| 1 | Normal |
| 2 | Abnormal, not clinically significant |
| 3 | Abnormal, clinically significant |
| 4 | Not assessed |

Facial Nerve Grading System: The Regional House-Brackmann Facial Nerve Grading System (see, Yen, T L, et al. Significance of House-Brackmann facial nerve grading global score in the setting of differential facial nerve function. *Otol Neurotol* 2003; 24(1):118-222, which is hereby incorporated by reference in its entirety) was designed to evaluate synkinesis and the four major branches of the facial nerve (VII) that innervates target and adjacent musculature. Functionality of the facial nerve (VII) was evaluated pre-application, day 2, and weeks 2, 4, and 8 (or early discontinuation). Examination procedures and criteria are set forth in Table 11.

TABLE 11

Regional House-Brackmann Facial Nerve Grading System

| Forehead | 1 | Normal forehead movement |
|---|---|---|
| | 2 | Slight weakness in forehead movement |
| | 3 | Obvious but not disfiguring asymmetry with motion, symmetric at rest |
| | 4 | Obvious weakness of disfiguring asymmetry with motion, symmetric at rest |
| | 5 | Barely perceptible motion in forehead, asymmetric at rest |
| | 6 | No movement |
| Eye | 1 | Normal eye closure |
| | 2 | Mild weakness in eye closure |
| | 3 | Obvious weakness but able to close eyes |
| | 4 | Unable to close eye with maximal effort |
| | 5 | Barely perceptible eyelid movement |
| | 6 | No movement |
| Midface | 1 | Normal midface movement |
| | 2 | Slight weakness in midface movement |
| | 3 | Obvious but not disfiguring weakness, symmetric at rest |
| | 4 | Obvious weakness and disfiguring asymmetry with motion, symmetric at rest |
| | 5 | Barely perceptible motion in midface, asymmetric at rest |
| | 6 | No movement |
| Mouth | 1 | Normal corner of mouth movement |
| | 2 | Slight weakness of corner of mouth movement |
| | 3 | Obvious but not disfiguring weakness, symmetric at rest |
| | 4 | Obvious weakness and disfiguring asymmetry with motion, symmetric at rest |
| | 5 | Barely perceptible corner of mouth movement, asymmetric at rest |
| | 6 | No movement |
| Synkinesis | 1 | None |
| | 2 | Mild - obvious but not disfiguring |
| | 3 | Severe - disfiguring or interferes with function |

Adverse Events: AEs were graded based on the CTEP-CTCAE version 4.03 for severity, where applicable. Otherwise AEs were graded as mild, moderate, severe, or life-threatening. AEs were evaluated post-application at treatment (day 0), and on follow-up visits at day 2 and weeks 2, 4, and 8 (or early discontinuation).

Safety Evaluations

Safety evaluations included the following tests:
clinical laboratory tests (hematology, chemistry, urinalysis) at screening and week 8;
local irritation of treatment areas at screening, treatment (day 0, pre- and post-application), day 2, and weeks 2, 4, and 8;
cranial nerves I-VII assessment including Regional House-Brackmann Facial Nerve Evaluation for cranial nerve VII at treatment (day 0, pre-application), day 2, and weeks 2, 4, and 8;
adverse events (AEs) from treatment (day 0) through final evaluation;
concomitant therapy/medication from screening through final evaluation; and
urine pregnancy test for women of childbearing potential at screening, treatment (day 0) and final evaluation.

All week 8 assessments were conducted at early discontinuation visit, as applicable.

Statistical Analysis

All statistical programming and analyses were performed using SAS, versin 9.1 or higher.

Populations: All randomized subjects were included in the summaries of demographic and other baseline characteristics. Efficacy analyses were carried out in the intent to treat (ITT) population, defined as all randomized subjects who received either the test article or placebo. When possible, the last observation carried forward (LOCF) approach was used to impute missing efficacy data. Per Protocol (PP) analyses were also performed. No imputations were utilized for the PP analyses. The safety population included all randomized subjects, exposed to either the test article or placebo, that provided any post-treatment safety information.

Efficacy Analyses: The primary efficacy endpoint was based on change from baseline in total nasal symptom score at week 4 for treatment versus control. Demonstration of efficacy required trending at p<0.20, rather than direct statistical significance at other thresholds given the sample size and study design. Comparisons were made using a 2 tailed t-test. Two interim analyses of efficacy were performed, the first when 4 week data became available for at least 30 subjects; and the second when 75% or more of subjects reached week 4 (or early study discontinuation).

Secondary endpoints included the following with statistical analyses, as with the primary endpoint, or by Inferential statistics based on the Fisher's exact test CMH, or Pearson Chi Square test.
  change from baseline to week 2, 4, and 8, respectively, in individual nasal symptom scores for rhinorrhea, nasal congestion, nasal itching and sneezing, recorded daily by subject and reported at visits (pre- and post-allergen challenge where applicable);
  change from baseline to week 2, 4, and 8, respectively in RQLQ; and
  PNIF and PEF at week 2, 4, and 8 respectively (pre- and post-allergen challenge where applicable).

Change from pre-treatment values also was evaluated. The difference between PNIF and PEF was calculated and examined by treatment as well ("PEF-PNIF differences").

Exploratory analyses using daily and mean weekly subject-recorded values also were conducted. Additional exploratory analyses evaluated composite endpoints based upon categories and definitions specified as primary or secondary endpoints above. These composites combined two endpoints, with response required on both simultaneously.

Safety Analyses: All treatment-emergent AEs occurring during the study were recorded and classified on the basis of MedDRA terminology for the safety population. Treatment-emergent AEs were summarized by treatment group, the number of subjects reporting treatment-emergent AEs, system organ class, preferred term, severity, relationship, and seriousness. Comparisons between treatment groups were made by tabulating the frequency of subjects with one or more treatment-emergent AEs during the study. The Fisher's exact test was used to compare the proportion of subjects in each treatment group who report any treatment-emergent AEs at a significance level of 0.05.

Serious adverse events (SAEs) also were listed by subject, and summarized by treatment group, severity, and relationship to study treatment.

Additional safety assessments, including clinical laboratory values and urine pregnancy tests, were summarized for all treated subjects by treatment group. Outcomes of the local irritation of treated areas assessments were tabulated by visit, along with the outcomes of the cranial nerves I-VII assessments. Concomitant therapies/medications used at screening and each study visit were also summarized.

Sample Size Justification: Approximately 70 subjects were enrolled and randomized 1:1 to either test article or placebo. Based upon an estimated 12% difference between treatment and placebo groups, based on historical data for injectable *botulinum* toxin type A, approximately 35 subjects per group were required to demonstrate trending toward efficacy (primary statistical analyses).

Results

Interim results when 75% or more of subjects reached week 4 are set forth below in Tables 12 and 13. Table 12 represents secondary efficacy analysis results, based on PEF-PNIF differences at week 4, in the ITT population. In this population, the within-group median was substituted for missing observations.

TABLE 12

| | | Treatment Group | | |
|---|---|---|---|---|
| | | Test Article (25 ng/ml) | Placebo Group | Total Subjects |
| Number of ITT Subjects | | 16 | 14 | 30 |
| Subjects Assessed by PNIF and PEF at Week 4 | | 16 | 14 | 30 |
| Mean (SD) pre-challenge PEF-PNIF difference at Week 4 | | 337.0 (96.31) | 433.2 (119.70) | 381.9 (116.64) |
| | p-value[1] | 0.0213 | | |
| Mean (SD) post-challenge PEF-PNIF difference at Week 4 | | 394.8 (130.71) | 444.9 (142.01) | 418.2 (136.11) |
| | p-value[1] | 0.3222 | | |

[1]p-value compares the treatment group to the placebo group using a two-sided t-test.

Table 13 represents secondary efficacy analysis results, based on post-challenge total nasal symptom (TNS) score at baseline (screening) and week 4, in the ITT population. In this population, the within-group median was substituted for missing observations.

TABLE 13

| | Treatment Group | | |
|---|---|---|---|
| | Formulation 24 (25 ng/ml) | Placebo Group | Total Subjects |
| Number of ITT Subjects | 16 | 14 | 30 |
| Subjects Assessed by Post-Challenge TNS at Baseline | 16 | 14 | 30 |

TABLE 13-continued

| | Treatment Group | | |
|---|---|---|---|
| | Formulation 24 (25 ng/ml) | Placebo Group | Total Subjects |
| Mean (SD) post-challenge TNS at baseline | 8.4 (2.42) | 8.6 (2.71) | 8.5 (2.52) |
| p-value[1] | 0.8873 | | |
| Subjects Assessed by Post-Challenge TNS at Week 4 | 16 | 14 | 30 |
| Mean (SD) post-challenge TNS at Week 4 | 4.4 (1.90) | 5.9 (3.70) | 5.1 (2.92) |
| p-value[2] | 0.2109 | | |
| Subjects Assessed by Post-Challenge TNS at Baseline and Week 4 | 16 | 14 | 30 |
| Mean (SD) absolute change from baseline in Post-Challenge TNS at Week 4 | 4.4 (1.90) | 5.9 (3.70) | 5.1 (2.92) |
| p-value[1] | 0.2167 | | |
| Mean (SD) percent change from baseline in Post-Challenge TNS at Week 4 | −3.8 (2.62) | −2.5 (2.79) | −3.2 (2.73) |
| p-value[1] | 0.3630 | | |

[1]p-value compares the treatment group to the placebo group using a two-sided t-test.

As shown in the Tables, total nasal symptom scores varied depending on subject and pollen count, whereas results after forced allergen challenge were more consistent. The results displayed a pattern consistent with the literature, in terms of the magnitude of an effective signal.

What is claimed is:

1. A method for treating rhinitis, the method comprising intranasally administering a therapeutically effective amount of a botulinum toxin composition to a patient in need of treatment; wherein said botulinum toxin composition comprises a purified 150 kDa botulinum neurotoxin isolated from botulinum toxin type A;

a carrier molecule comprising a polypeptide having the amino acid sequence RKKRRQRRR-Q-$(K)_{15}$-Q-RK-KRRQRRR (SEQ ID NO: 18); and a viscosity modifier in the form of a gel or a solution that forms a gel upon an increase in temperature;

wherein said intranasal administration provides a dose of the purified botulinum neurotoxin of 250 U to 12,500 U to said patient.

2. The method according to claim 1 wherein said intranasal administration provides a dose of the purified botulinum neurotoxin of about 1,250 U to said patient.

3. The method according to claim 1, wherein the concentration of said botulinum toxin composition is 6,250 U/mL.

4. The method according to claim 1, wherein the viscosity modifier agent is poloxamer 407.

5. The method according to claim 1, wherein said composition is applied using a single intranasal application for a duration of 5 seconds to 60 minutes.

6. The method according to claim 1, wherein said composition is applied using a single intranasal application for a duration of 30 seconds to 45 minutes.

7. The method according to claim 1, wherein said composition is applied using a single intranasal application for a duration of 1 minute to 30 minutes.

8. The method according to claim 1, wherein said composition is applied using a single intranasal application for a duration of 30 minutes.

\* \* \* \* \*

SEQUENCE LISTING

```
<160> NUMBER OF SEQ ID NOS: 18

<210> SEQ ID NO 1
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(20)
<223> OTHER INFORMATION: This region may encompass 0-20 'Gly' residues
<220> FEATURE:
<221> NAME/KEY: misc_feature
<222> LOCATION: (21)..(45)
<223> OTHER INFORMATION: This region may encompass 5-25 'Arg' residues
<220> FEATURE:
<223> OTHER INFORMATION: See specification as filed for detailed
      description of substitutions and preferred embodiments

<400> SEQUENCE: 1

Gly Gly Gly Gly Gly Gly Gly Gly Gly Gly Gly Gly Gly Gly Gly
1               5                   10                  15

Gly Gly Gly Gly Arg Arg Arg Arg Arg Arg Arg Arg Arg Arg Arg
                20                  25                  30

Arg Arg Arg Arg Arg Arg Arg Arg Arg Arg Arg Arg Arg
                35                  40                  45

<210> SEQ ID NO 2
<211> LENGTH: 51
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(20)
<223> OTHER INFORMATION: This region may encompass 0-20 'Gly' residues
<220> FEATURE:
```

```
<221> NAME/KEY: misc_feature
<222> LOCATION: (32)..(51)
<223> OTHER INFORMATION: This region may encompass 0-20 'Gly' residues
<220> FEATURE:
<223> OTHER INFORMATION: See specification as filed for detailed
      description of substitutions and preferred embodiments

<400> SEQUENCE: 2

Gly Gly Gly Gly Gly Gly Gly Gly Gly Gly Gly Gly Gly Gly Gly Gly
1               5                   10                  15

Gly Gly Gly Gly Arg Gly Arg Asp Asp Arg Arg Gln Arg Arg Arg Gly
            20                  25                  30

Gly Gly Gly Gly Gly Gly Gly Gly Gly Gly Gly Gly Gly Gly Gly Gly
        35                  40                  45

Gly Gly Gly
    50

<210> SEQ ID NO 3
<211> LENGTH: 51
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(20)
<223> OTHER INFORMATION: This region may encompass 0-20 'Gly' residues
<220> FEATURE:
<221> NAME/KEY: misc_feature
<222> LOCATION: (32)..(51)
<223> OTHER INFORMATION: This region may encompass 0-20 'Gly' residues
<220> FEATURE:
<223> OTHER INFORMATION: See specification as filed for detailed
      description of substitutions and preferred embodiments

<400> SEQUENCE: 3

Gly Gly Gly Gly Gly Gly Gly Gly Gly Gly Gly Gly Gly Gly Gly Gly
1               5                   10                  15

Gly Gly Gly Gly Tyr Gly Arg Lys Lys Arg Arg Gln Arg Arg Arg Gly
            20                  25                  30

Gly Gly Gly Gly Gly Gly Gly Gly Gly Gly Gly Gly Gly Gly Gly Gly
        35                  40                  45

Gly Gly Gly
    50

<210> SEQ ID NO 4
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(20)
<223> OTHER INFORMATION: This region may encompass 0-20 'Gly' residues
<220> FEATURE:
<221> NAME/KEY: misc_feature
<222> LOCATION: (30)..(49)
<223> OTHER INFORMATION: This region may encompass 0-20 'Gly' residues
<220> FEATURE:
<223> OTHER INFORMATION: See specification as filed for detailed
      description of substitutions and preferred embodiments

<400> SEQUENCE: 4

Gly Gly Gly Gly Gly Gly Gly Gly Gly Gly Gly Gly Gly Gly Gly Gly
1               5                   10                  15
```

Gly Gly Gly Gly Arg Lys Lys Arg Arg Gln Arg Arg Gly Gly Gly
                    20                  25                  30

Gly Gly Gly Gly Gly Gly Gly Gly Gly Gly Gly Gly Gly
            35                  40                  45

Gly

<210> SEQ ID NO 5
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Arg Lys Lys Arg Arg Gln Arg Arg Gly Lys Lys Lys Lys Lys Lys
1               5                   10                  15

Lys Lys Lys Lys Lys Lys Lys Lys Lys Gly Arg Lys Lys Arg Arg Gln
                20                  25                  30

Arg Arg Arg
        35

<210> SEQ ID NO 6
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Arg Lys Lys Arg Arg Gln Arg Arg Gly Lys Lys Lys Lys Lys Lys
1               5                   10                  15

Lys Lys Lys Lys Lys Lys Lys Lys Lys Lys Lys Lys Lys Gly Arg
                20                  25                  30

Lys Lys Arg Arg Gln Arg Arg Arg
        35                  40

<210> SEQ ID NO 7
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Arg Lys Lys Arg Arg Gln Arg Arg Gly Lys Lys Lys Lys Lys Lys
1               5                   10                  15

Lys Lys Lys Lys Lys Lys Lys Lys Lys Lys Lys Lys Lys Lys Lys
                20                  25                  30

Lys Lys Lys Gly Arg Lys Lys Arg Arg Gln Arg Arg
        35                  40                  45

<210> SEQ ID NO 8
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Arg Lys Lys Arg Arg Gln Arg Arg Gly Lys Lys Lys Lys Lys
1               5                   10                  15

Lys Lys Lys Lys Lys Lys Lys Lys Lys Lys Lys Lys Lys Lys Lys
            20                  25                  30

Lys Lys Lys Lys Lys Lys Lys Gly Arg Lys Arg Arg Gln Arg
        35                  40                  45

Arg Arg
    50

<210> SEQ ID NO 9
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Arg Gly Arg Asp Asp Arg Arg Gln Arg Arg Gly Lys Lys Lys
1               5                   10                  15

Lys Lys Lys Lys Lys Lys Lys Lys Lys Lys Gly Arg Gly Arg Asp
            20                  25                  30

Asp Arg Arg Gln Arg Arg Arg
        35

<210> SEQ ID NO 10
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Arg Gly Arg Asp Asp Arg Arg Gln Arg Arg Gly Lys Lys Lys Lys
1               5                   10                  15

Lys Lys Lys Lys Lys Lys Lys Lys Lys Lys Lys Lys Lys Lys Lys
            20                  25                  30

Gly Arg Gly Arg Asp Asp Arg Arg Gln Arg Arg Arg
        35                  40

<210> SEQ ID NO 11
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Arg Gly Arg Asp Asp Arg Arg Gln Arg Arg Gly Lys Lys Lys Lys
1               5                   10                  15

Lys Lys Lys Lys Lys Lys Lys Lys Lys Lys Lys Lys Lys Lys Lys
            20                  25                  30

Lys Lys Lys Lys Lys Gly Arg Gly Arg Asp Asp Arg Arg Gln Arg Arg
        35                  40                  45

Arg

<210> SEQ ID NO 12
<211> LENGTH: 54
<212> TYPE: PRT

<213> ORGANISM: Artificial Sequence
<220> FEATURE:
<223> OTHER INFORMATION: Description of Artificial Sequence: Synthetic
     polypeptide

<400> SEQUENCE: 12

Arg Gly Arg Asp Asp Arg Arg Gln Arg Arg Gly Lys Lys Lys
1               5                  10                  15

Lys Lys Lys Lys Lys Lys Lys Lys Lys Lys Lys Lys Lys Lys
            20                  25                  30

Lys Lys Lys Lys Lys Lys Lys Lys Gly Arg Gly Arg Asp Asp
        35                  40                  45

Arg Arg Gln Arg Arg Arg
        50

<210> SEQ ID NO 13
<211> LENGTH: 39
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 13

Tyr Gly Arg Lys Lys Arg Arg Gln Arg Arg Gly Lys Lys Lys
1               5                  10                  15

Lys Lys Lys Lys Lys Lys Lys Lys Lys Lys Gly Tyr Gly Arg Lys
            20                  25                  30

Lys Arg Arg Gln Arg Arg Arg
        35

<210> SEQ ID NO 14
<211> LENGTH: 44
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 14

Tyr Gly Arg Lys Lys Arg Arg Gln Arg Arg Gly Lys Lys Lys
1               5                  10                  15

Lys Lys Lys Lys Lys Lys Lys Lys Lys Lys Lys Lys Lys Lys
            20                  25                  30

Gly Tyr Gly Arg Lys Lys Arg Arg Gln Arg Arg Arg
        35                  40

<210> SEQ ID NO 15
<211> LENGTH: 49
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 15

Tyr Gly Arg Lys Lys Arg Arg Gln Arg Arg Gly Lys Lys Lys
1               5                  10                  15

Lys Lys Lys Lys Lys Lys Lys Lys Lys Lys Lys Lys Lys Lys
            20                  25                  30

Lys Lys Lys Lys Lys Gly Tyr Gly Arg Lys Lys Arg Arg Gln Arg Arg
        35                  40                  45

Arg

```
<210> SEQ ID NO 16
<211> LENGTH: 54
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Tyr Gly Arg Lys Lys Arg Arg Gln Arg Arg Gly Lys Lys Lys Lys
1               5                   10                  15

Lys Lys Lys Lys Lys Lys Lys Lys Lys Lys Lys Lys Lys Lys Lys
            20                  25                  30

Lys Lys Lys Lys Lys Lys Lys Lys Lys Gly Tyr Gly Arg Lys Lys
        35                  40                  45

Arg Arg Gln Arg Arg Arg
        50

<210> SEQ ID NO 17
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Gly Gly Arg Arg Arg Arg Arg Arg Arg
1               5                   10

<210> SEQ ID NO 18
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Arg Lys Lys Arg Arg Gln Arg Arg Arg Gln Lys Lys Lys Lys Lys
1               5                   10                  15

Lys Lys Lys Lys Lys Lys Lys Lys Lys Gln Arg Lys Lys Arg Arg Gln
            20                  25                  30

Arg Arg Arg
        35
```